(12) United States Patent
Takayama et al.

(10) Patent No.: US 9,377,404 B2
(45) Date of Patent: Jun. 28, 2016

(54) PLANT HEALTH DIAGNOSTIC METHOD AND PLANT HEALTH DIAGNOSTIC DEVICE

(75) Inventors: Kotaro Takayama, Matsuyama (JP); Hiroshige Nishina, Matsuyama (JP); Soushi Iyoki, Matsuyama (JP)

(73) Assignee: NATIONAL UNIVERSITY CORPORATION EHIME UNIVERSITY, Ehime (JP)

( * ) Notice: Subject to any disclaimer, the term of this patent is extended or adjusted under 35 U.S.C. 154(b) by 203 days.

(21) Appl. No.: 13/880,930

(22) PCT Filed: Nov. 7, 2011

(86) PCT No.: PCT/JP2011/006197
§ 371 (c)(1),
(2), (4) Date: Jun. 21, 2013

(87) PCT Pub. No.: WO2012/063455
PCT Pub. Date: May 18, 2012

(65) Prior Publication Data
US 2013/0276368 A1    Oct. 24, 2013

(30) Foreign Application Priority Data

Nov. 8, 2010    (JP) ................................ 2010-250098

(51) Int. Cl.
*G06K 9/00*    (2006.01)
*G01N 21/64*    (2006.01)
(Continued)

(52) U.S. Cl.
CPC ........ *G01N 21/64* (2013.01); *A01G 7/00* (2013.01); *G01N 21/6408* (2013.01); *G01N 21/6456* (2013.01); *G06T 7/0002* (2013.01); *G01N 2021/635* (2013.01)

(58) Field of Classification Search
CPC ............... G06T 7/0002; G06T 2207/30128; G06T 7/0004
USPC ....................................................... 382/110
See application file for complete search history.

(56) References Cited

U.S. PATENT DOCUMENTS

2001/0036295 A1* 11/2001 Hendrickson et al. ........ 382/110
2008/0304711 A1* 12/2008 Scharf et al. .................. 382/110
(Continued)

FOREIGN PATENT DOCUMENTS

JP    2001-299090 A    10/2001
JP    2002-214141 A    7/2002

OTHER PUBLICATIONS

International Search Report for the Application No. PCT/JP2011/006197 mailed Dec. 20, 2011.
(Continued)

*Primary Examiner* — Samir Ahmed
(74) *Attorney, Agent, or Firm* — Cheng Law Group, PLLC

(57) ABSTRACT

This invention provides a plant health diagnostic method and a plant health diagnostic device for detecting initial disorder of a plant individual body carrying pests or the like in a large-scale plant cultivation field. The plant health diagnostic method is for diagnosing a health state of a plant in accordance with chlorophyll fluorescence emitted from chlorophyll of a plant body. The method includes: obtaining a first minimum point s after a maximum point p having largest chlorophyll fluorescence intensity and a first maximum point m after the minimum point s on a time course curve for the chlorophyll fluorescence intensity; defining chlorophyll fluorescence intensity values at the minimum point s and the first maximum point m after the minimum point s as S and M, respectively; and comparing the value S and the value M to evaluate the state of the plant. The state of the plant, which cannot be visually recognized from outer appearance, can be detected by comparison between the chlorophyll fluorescence intensity values (S and M), thereby realizing diagnosis of the state of the plant individual body in an early stage.

14 Claims, 9 Drawing Sheets

(51) Int. Cl.
  *A01G 7/00* (2006.01)
  *G06T 7/00* (2006.01)
  *G01N 21/63* (2006.01)

(56) References Cited

U.S. PATENT DOCUMENTS

2009/0260281 A1* 10/2009 Conrad .............................. 47/14
2011/0286636 A1* 11/2011 Purcell et al. ................. 382/110

OTHER PUBLICATIONS

International Preliminary Report on Patentability (PCT/IPEA/409) for Application No. PCT/JP2011/006197 dated Feb. 12, 2013.

Written Opinion of the International Searching Authority (PCT/IPEA/408) for Application No. PCT/JP2011/006197 mailed Sep. 4, 2012.
Written Opinion of the International Searching Authority (PCT/ISA/237) for Application No. PCT/JP2011/006197 mailed Dec. 20, 2011.
Takayama, Kotaro et al., "Health State Monitoring on Tomato Cluster by Chlorophyll Fluorescence Image Measurement", Japanese Society of Agricultural, Biological and Enviromental Engineers and Scientists, 2009. pp. 94-95.
Takayama, Kotaro et al., "Detection of Tomato Russet Mite Damage in Early Stage by Chlorophyll Fluorescence Image Measurement", Japanese Society of Agricultural, Biological and Environmental Engineers and Scientists, 2010, pp. 28-29.

* cited by examiner (A)

(B)

(A)

(B)

(C)

(A)

(B)

(C)

PLANT HEALTH DIAGNOSTIC METHOD AND PLANT HEALTH DIAGNOSTIC DEVICE

TECHNICAL FIELD

The present invention relates to a plant health diagnostic method and a plant health diagnostic device. More particularly, the present invention relates to a plant health diagnostic method and a plant health diagnostic device for detecting initial disorder in physiological function of a plant due to pests such as tomato russet mite and removing in an early stage so as to keep a stable crop yield and stable quality.

BACKGROUND ART

Conventionally, in a plant cultivation field, a producer or the like has visually observed leaves of cultivated plants in order to check health states of the plants, and has removed disordered portions (such as leaves) that are damaged by pests or the like.

In recent years, a cultivation method of cultivating plants in a large scale has become popular, with increase in cultivation area. If the cultivation area increases, a producer or the like has difficulty in managing health states entirely in a cultivated plant cluster in the manner similar to the conventional method (removal of disordered sites by visual observation, for example).

There has been proposed a technique of diagnosing a health state of a plant in terms of a physiological function of the plant, with no visual observation.

For example, there is a technique of managing a health state of a plant by evaluating a photosynthetic function, which is closely relevant to the health state of the plant. In this technique, photochemical reaction is driven by light energy absorbed by chlorophyll, and chlorophyll fluorescence emitted by the chlorophyll is measured to quantitatively evaluate the photosynthetic function in the plant. This technique is referred to as the chlorophyll fluorescence image measurement method because chlorophyll fluorescence is measured by means of an image. In this chlorophyll fluorescence image measurement method, chlorophyll fluorescence emitted by chlorophyll that is important in photosynthesis is measured. It is thus possible to directly diagnose photosynthetic reaction. Accordingly, physiological functional disorder of a plant, in other words, invisible disorder from outer appearance, can be diagnosed.

For example, Patent Documents 1 and 2 each disclose a technique of diagnosing a health state of a plant in accordance with this chlorophyll fluorescence image measurement method.

Patent Document 1 discloses a technique of diagnosing a growth state of a plant by irradiating the plant with laser light and measuring laser excited fluorescence released from a leaf of the plant.

According to Patent Document 1, the health state of the target plant can be diagnosed by measuring chlorophyll fluorescence of a predetermined wavelength released from the leaf having received laser light and comparing a measurement value with a reference value of a healthy plant and a reference value indicating a growth limit of withering or the like. These reference values are set preliminarily.

Patent Document 2 describes diagnosis of a health state of a plant by measuring chlorophyll fluorescence of a predetermined wavelength released from a leaf having received laser light and estimating a chlorophyll content in the target plant from a measurement value in accordance with a calibration curve that is formed preliminarily and indicates the relationship between chlorophyll concentration in a healthy plant and chlorophyll fluorescence.

In the large-scale cultivation method in recent years, plants of a same breed are cultivated in a large scale. If one of the plant individual bodies carries pests, damage rapidly expands to other adjacent plant individual bodies. With slight delay in taking action, there is a risk of expansion of pests entirely in the cultivated plant cluster. If the cultivated plant has pests or the like, fruits obtained from this plant decrease in crop yield and quality in comparison to those obtained from a healthy plant individual body, thereby causing a huge loss to a producer and the like.

In particular, tomato russet mite as one type of rust mites are common pests that appear throughout a year in structured cultivation and wither stems and leaves, while fruits are damaged to have rough skins. Such tomato russet mite have extraordinary high biotic potential and rapidly expand to other adjacent plant individual bodies in a few days. Detection in an early stage is important for inhibition of damage.

At the initial stage of appearance of the pests, leaves and the like do not have disorder such as withering. It is thus impossible to recognize damage from outer appearance. Damage cannot be recognized from outer appearance until a stage of expansion of the damage to some extent, in other words, until tomato russet mite expand from a plant individual body to other adjacent plant individual bodies.

Meanwhile, tomato russet mite are highly sensitive to agricultural chemicals and can be easily removed by spraying a small amount of an agricultural chemical to a plant individual body having initial damage if such a plant individual body having initial damage can be detected. In order to inhibit disorder by tomato russet mite, it is quite important to detect appearance and remove tomato russet mite in an early stage. This applies also to other pests that rapidly expand to other adjacent plant individual bodies in a few days with high biotic potential and are highly sensitive to agricultural chemicals.

Upon such removal, it is possible to apply the technique of Patent Document 1 or 2 for detection of a plant individual body having pests or the like. These techniques enable detection of a withered plant individual body but cannot achieve detection of a plant individual body carrying pests or the like in an initial stage.

Currently, there is developed no diagnostic method that achieves detection of disorder in an initial stage of a plant individual body having pests or the like. Desired therefore is development of a plant health diagnostic method in an early stage, which is applicable to the plant cultivation method with a large cultivation area.

PRIOR ART DOCUMENTS

Patent Documents

Patent Document 1: JP 2001-299090 A
Patent Document 2: JP 2002-214141 A

SUMMARY OF THE INVENTION

Problems to be Solved by the Invention

In view of the circumstances mentioned above, it is an object of the present invention to provide a plant health diagnostic method and a plant health diagnostic device for detecting initial disorder of a plant individual body carrying pests or the like.

Means for Solving the Problems

According to a first invention, in a plant health diagnostic method of diagnosing a health state of a plant in accordance with chlorophyll fluorescence emitted from chlorophyll of a plant body, the method includes: obtaining a first minimum point after a maximum point having largest chlorophyll fluorescence intensity and a first maximum point after the minimum point on a time course curve of the chlorophyll fluorescence intensity; defining chlorophyll fluorescence intensity values at the minimum point and the first maximum point after the minimum point as S and M, respectively; obtaining a value M/S from the values S and M; and evaluating an initial state of photosynthetic functional disorder of the plant body with use of the value M/S and a value M/S of a healthy site of a plant body or of a healthy plant individual body as a reference value.

According to a second invention, in the first invention, the plant health diagnostic method further includes: obtaining the maximum point having the largest chlorophyll fluorescence intensity on the time course curve of the chlorophyll fluorescence intensity; defining a chlorophyll fluorescence intensity value at the maximum point having the largest chlorophyll fluorescence intensity as P; obtaining a value P/S from the values P and S; and evaluating an initial state of photosynthetic functional disorder of the plant body with use of the value P/S and a value P/S of a healthy site of a plant body or of a healthy plant individual body as a reference value.

In the plant health diagnostic method according to a third invention, in the first and second inventions, the initial state of photosynthetic functional disorder is not visually detected.

According to a fourth invention, in a plant health diagnostic device for diagnosing a health state of a plant in accordance with chlorophyll fluorescence emitted from chlorophyll of a plant body, the device includes: fluorescence measurement means for measuring intensity of the chlorophyll fluorescence; and analysis means for evaluating the state of the plant in accordance with the chlorophyll fluorescence intensity measured by the fluorescence measurement means; wherein the analysis means obtains a first minimum point after a maximum point having largest chlorophyll fluorescence intensity and a first maximum point after the minimum point on a time course curve of the chlorophyll fluorescence intensity measured by the fluorescence measurement means, defines chlorophyll fluorescence intensity values at the minimum point and the first maximum point after the minimum point as S and M, respectively, obtains a value M/S from the values S and M, and evaluates an initial state of photosynthetic functional disorder of the plant body with use of the value M/S and a value M/S of a healthy site of a plant body or of a healthy plant individual body as a reference value.

In the plant health diagnostic device according to a fifth invention, in the fourth invention, the analysis means obtains the maximum point having the largest chlorophyll fluorescence intensity on the time course curve of the chlorophyll fluorescence intensity measured by the fluorescence measurement means, defines a chlorophyll fluorescence intensity value at the maximum point as P, obtains a value P/S from the values P and S, and evaluates an initial state of photosynthetic functional disorder of the plant body with use of the value P/S and a value P/S of a healthy site of a plant body or of a healthy plant individual body as a reference value.

In the plant health diagnostic device according to a sixth invention, in the fourth or fifth invention, the fluorescence measurement means measures the chlorophyll fluorescence intensity as an image, and the analysis means forms an M/S image and/or a P/S image configured by the value M/S and/or the value P/S in accordance with the image of the measured chlorophyll fluorescence intensity, and evaluates an initial state of photosynthetic functional disorder of the plant body with use of the M/S image and/or the P/S image thus formed and an M/S image and/or a P/S image of a healthy site of a plant body or of a healthy plant individual body as a reference image.

In the plant health diagnostic device according to a seventh invention, in the fourth to sixth inventions, the initial state of photosynthetic functional disorder is not visually detected.

According to an eighth invention, in a plant health diagnostic method of diagnosing a health state of a plant in accordance with chlorophyll fluorescence emitted from chlorophyll of a plant body, the method includes: obtaining a first minimum point after a maximum point having largest chlorophyll fluorescence intensity and a first maximum point after the minimum point on a time course curve of the chlorophyll fluorescence intensity; defining chlorophyll fluorescence intensity values at the minimum point and the first maximum point after the minimum point as S and M, respectively; obtaining a value M/S from the values S and M; discriminating a leaf portion and a stem portion in the plant with use of the value M/S; and diagnosing a growth state of the plant in accordance with a stem diameter of the discriminated stem portion.

According to a ninth invention, in the eighth invention, the plant health diagnostic method further includes: obtaining the maximum point having the largest chlorophyll fluorescence intensity on the time course curve of the chlorophyll fluorescence intensity; defining a chlorophyll fluorescence intensity value at the maximum point having the largest chlorophyll fluorescence intensity as P; obtaining a value P/S from the values P and S; discriminating a leaf portion and a stem portion in the plant with use of the value P/S; and diagnosing a growth state of the plant in accordance with a stem diameter of the discriminated stem portion.

Effects of the Invention

According to the first invention, the chlorophyll fluorescence intensity values (M and S) are calculated in accordance with the time course curve of the chlorophyll fluorescence intensity of the plant individual body, and the value M/S is calculated from the calculated chlorophyll fluorescence intensity values (M and S). The state of the plant (such as change in state or a difference of the plant), which cannot be recognized from outer appearance, can be detected by evaluating the state of the plant in accordance with the value M/S. It is thus possible to diagnose the state of the plant individual body (such as change in growth state of the plant individual body) in an early stage. Thanks to detection of the plant individual body carrying pests or the like in an initial stage, it is possible to remove such pests or the like in an early stage by spraying a small amount of an agricultural chemical only to the plant individual body, thereby preventing expansion of pests or the like in an entire plant cluster. The chlorophyll fluorescence intensity values (M and S) at each site of the plant individual body are calculated, and the value M/S is calculated from the calculated chlorophyll fluorescence intensity values (M and S). It is then possible to discriminate between the stem portion and the leaf portion in accordance with the values M/S. In this case, it is possible to find a growth state of the plant individual body from a stem diameter, and the plant individual body can be treated appropriately. In a plant production field, it is thus possible to produce plants of stable sizes and stably crop fruits and the like in the entire plant cluster. Furthermore, it is possible to distinguish a slight difference in photosynthetic function by evaluation of the photosynthetic function of the plant in accordance with the value M/S, thereby achieving more reliable evaluation of the state of the plant.

According to the second invention, the chlorophyll fluorescence intensity values (P and S) are calculated in accordance with the time course curve of the chlorophyll fluorescence intensity of the plant individual body, and the value P/S is calculated from the calculated chlorophyll fluorescence intensity values (P and S). The state of the plant, which cannot be recognized from outer appearance, can be detected by evaluation of the state of the plant in accordance with the value P/S. Furthermore, it is possible to reliably find the stem portion of the plant individual body in accordance with the maximum point of the largest chlorophyll fluorescence intensity, which can be reliably calculated from the time course curve of the chlorophyll fluorescence intensity of the plant individual body. In this case, it is possible to find a growth state of the plant individual body from a stem diameter, and the plant individual body can be treated appropriately. In a plant production field, it is thus possible to produce plants of stable sizes and stably crop fruits and the like in the entire plant cluster.

According to the third invention, it is possible to more reliably evaluate the state of the plant, such as change in state of the plant individual body, which is difficult to be visually found.

According to the fourth invention, the analysis means forms the time course curve of the chlorophyll fluorescence intensity at the measured site of the plant body from the chlorophyll fluorescence measured by the fluorescence measurement means. Furthermore, the analysis means calculates the chlorophyll fluorescence intensity values (M and S) in accordance with this time course curve, and calculates the value M/S from the chlorophyll fluorescence intensity values (M and S) thus calculated. The state of the plant is diagnosed in accordance with the value M/S. It is possible to detect the state of the plant (such as change in state or a difference of the plant), which cannot be recognized from outer appearance. It is thus possible to diagnose the state of the plant individual body (such as change in growth state of the plant individual body) in an early stage. Thanks to detection of the plant individual body carrying pests or the like in an initial stage, it is possible to remove such pests or the like in an early stage by spraying a small amount of an agricultural chemical only to the plant individual body, thereby preventing expansion of pests or the like in an entire plant cluster. The chlorophyll fluorescence intensity values (M and S) at each site of the plant individual body are calculated, and the value M/S is calculated from the calculated chlorophyll fluorescence intensity values (M and S). It is then possible to discriminate between the stem portion and the leaf portion in accordance with the values M/S. In this case, it is possible to find a growth state of the plant individual body from a stem diameter, and the plant individual body can be treated appropriately. In a plant production field, it is thus possible to produce plants of stable sizes and stably crop fruits and the like in the entire plant cluster. Furthermore, by evaluation of the photosynthetic function of the plant in accordance with the value M/S, it is possible to achieve more reliable evaluation of the state of the plant.

According to the fifth invention, the analysis means forms the time course curve of the chlorophyll fluorescence intensity at the measured site of the plant body from the chlorophyll fluorescence measured by the fluorescence measurement means. Furthermore, the analysis means calculates the chlorophyll fluorescence intensity values (P and S) in accordance with this time course curve, and calculates the value P/S from the chlorophyll fluorescence intensity values (P and S) thus calculated. The state of the plant, which cannot be recognized from outer appearance, can be detected by evaluation of the state of the plant in accordance with the value P/S. It is also possible to discriminate between the stem portion and the leaf portion because the maximum point p of the largest chlorophyll fluorescence intensity can be calculated reliably on the time course curve of the chlorophyll fluorescence intensity of the plant individual body. In this case, it is possible to find a growth state of the plant individual body from a stem diameter, and the plant individual body can be treated appropriately. In a plant production field, it is thus possible to produce plants of stable sizes and stably crop fruits and the like in the entire plant cluster.

According to the sixth invention, in accordance with the chlorophyll fluorescence measured as the image, it is possible to form the image (the M/S image or/and the P/S image) configuring the chlorophyll fluorescence image with use of the value M/S or/and the value P/S calculated for each pixel configuring the image. With use of the M/S image or/and the P/S image, it is then possible to find the state of the plant individual body, which cannot be found by direct visual checking.

According to the seventh invention, it is possible to more reliably evaluate the state of the plant, such as change in state of the plant individual body, which is difficult to be visually found.

According to the eighth invention, the chlorophyll fluorescence intensity values (M and S) are calculated in accordance with the time course curve of the chlorophyll fluorescence intensity of the plant individual body, and the value M/S is calculated from the calculated chlorophyll fluorescence intensity values (M and S). The state of the plant (such as change in state or a difference of the plant), which cannot be recognized from outer appearance, can be detected by evaluating the state of the plant in accordance with the value M/S. It is thus possible to diagnose the state of the plant individual body (such as change in growth state of the plant individual body) in an early stage. The chlorophyll fluorescence intensity values (M and S) at each site of the plant individual body are calculated, and the value M/S is calculated from the calculated chlorophyll fluorescence intensity values (M and S). It is then possible to discriminate between the stem portion and the leaf portion in accordance with the values M/S. In this case, it is possible to find a growth state of the plant individual body from a stem diameter, and the plant individual body can be treated appropriately. In other words, the leaf portion and the stem portion in the plant are discriminated from each other. It is thus possible to measure thickness of the stem portion (stem diameter) of each plant individual body. It is possible to find thickness of the stem portion (stem diameter), which is an important index for diagnosis of the growth state of the plant, thereby achieving evaluation of the health state of the plant individual body. In a plant production field, it is thus possible to produce plants of stable sizes and stably crop fruits and the like in the entire plant cluster.

According to the ninth invention, the chlorophyll fluorescence intensity values (P and S) are calculated in accordance with the time course curve of the chlorophyll fluorescence intensity of the plant individual body, and the value P/S is calculated from the calculated chlorophyll fluorescence intensity values (P and S). The state of the plant, which cannot be recognized from outer appearance, can be detected by evaluation of the state of the plant in accordance with the value P/S. Furthermore, it is possible to reliably find the stem portion of the plant individual body in accordance with the maximum point of the largest chlorophyll fluorescence intensity, which can be reliably calculated from the time course curve of the chlorophyll fluorescence intensity of the plant individual body. In other words, the leaf portion and the stem portion in the plant are discriminated from each other. It is thus possible to measure thickness of the stem portion (stem diameter) of each plant individual body. In this case, it is possible to find a growth state of the plant individual body from a stem diameter, and the plant individual body can be treated appropriately. In a plant production field, it is thus possible to produce plants of stable sizes and stably crop fruits and the like in the entire plant cluster.

BRIEF DESCRIPTION OF THE DRAWINGS

FIGS. 4(A) and 4(B) are explanatory conceptual diagrams of M/S images obtained by the device according to the present embodiment, in which FIG. 4(A) is a conceptual diagram of a visible image, and FIG. 4(B) is a conceptual diagram of an M/S image of a region same as a region shown in FIG. 4(A).

MODE FOR CARRYING OUT THE INVENTION

Described next is an embodiment of the present invention.

Briefly described first are a plant diagnostic device and a plant diagnostic method according to the present invention.

Important indices indicating whether or not a plant is healthy include soundness of a photosynthetic function of the plant. Photosynthesis of a plant starts with driving photochemical reaction by means of light energy absorbed by chlorophyll, while the light energy thus absorbed is not entirely applied to the photosynthesis. The absorbed light energy is partially released as chlorophyll fluorescence. By accurate measurement of intensity of this chlorophyll fluorescence (hereinafter, referred to as chlorophyll fluorescence intensity) and numerical evaluation, it is possible to accurately find a physiological function, more specifically, a photosynthetic function, in a plant body. Such a function cannot be visually recognized from outer appearance. In other words, by accurately measuring, numerically converting, and evaluating the chlorophyll fluorescence intensity, it is possible to detect slight state change of a plant, which cannot be understood by visual observation, with no damage to the plant or no contact with the plant.

Described next is the plant diagnostic device according to the present invention.

The plant diagnostic device according to the present invention diagnoses a health state of a plant in accordance with chlorophyll fluorescence, and is characterized by calculating a specific parameter from measured chlorophyll fluorescence intensity and numerically converting so as to detect the state of the plant in an early stage.

More specifically, the plant diagnostic device is characterized by numerically converting the health state of the plant (such as a plant body having a sound photosynthetic function) in order to detect poor growth, malfunction, or the like of the plant in an early stage.

Figure 2:
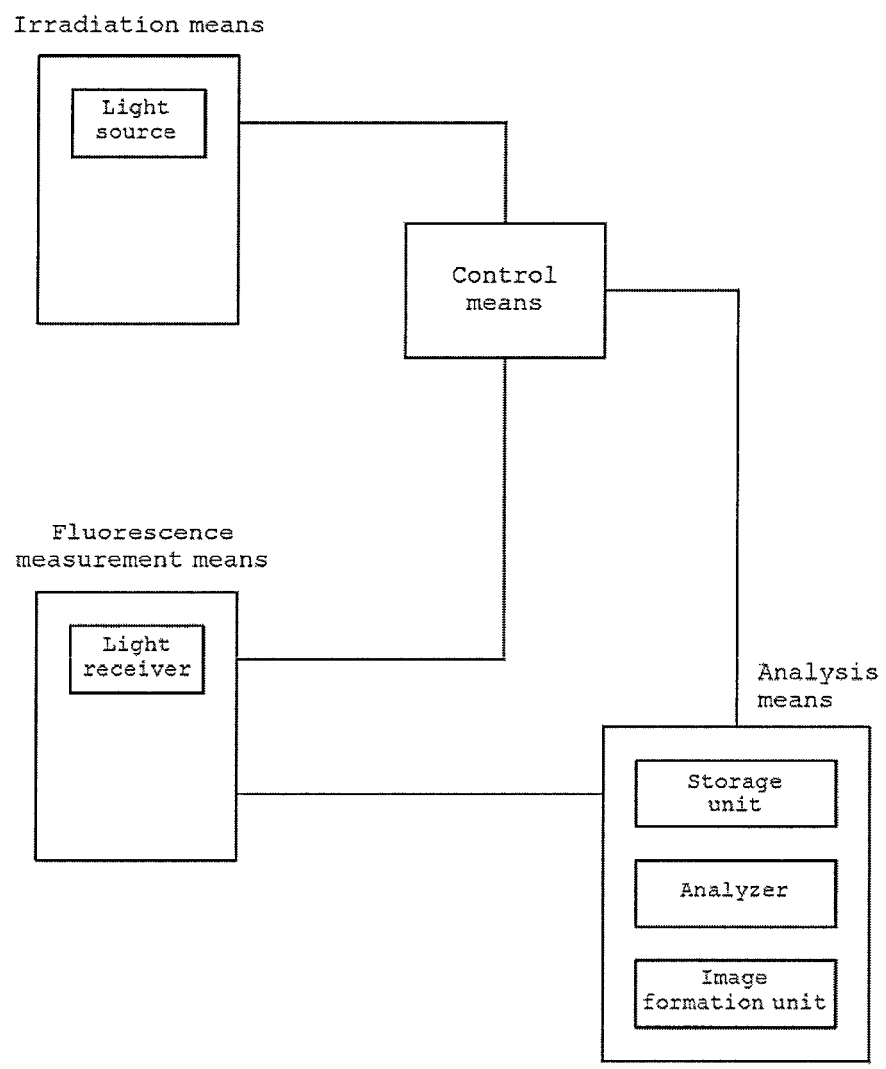
FIG. 2 is a conceptual diagram of a plant diagnostic device according to an embodiment.

A shown in FIG. 2, the plant diagnostic device according to the present invention includes fluorescence measurement means for measuring chlorophyll fluorescence emitted by chlorophyll upon irradiating a plant body with excitation light of constant intensity, and analysis means for analyzing intensity of chlorophyll fluorescence measured by the fluorescence measurement means and numerically converting to evaluate a state of the plant from the analysis result. Chlorophyll fluorescence is preferably measured under a dark condition at least one hour later from sunset, for example. Under this condition, it is possible to evaluate the photosynthetic function even when the excitation light for the chlorophyll fluorescence is weak.

(Description of Fluorescence Measurement Means)

The fluorescence measurement means includes a light receiver that is capable of measuring chlorophyll fluorescence emitted by chlorophyll having absorbed excitation light. This light receiver is not particularly limited as long as it is capable of detecting time course of chlorophyll fluorescence. Examples of the light receiver include a CCD camera and a photosensor filtered with a long-pass filter, which cuts the reflection of the excitaition light but allows to transmit the chlorophyll fluourescece.

(Example of Light Receiver)

Use of a CCD camera as the light receiver enables measurement of a phenomenon of emitting chlorophyll fluorescence by means of an image, thereby resulting in advantageous measurement of a large number of points at one time.

Use of a supersensitive CCD camera as the light receiver realizes detection of weak emission of chlorophyll fluorescence from chlorophyll. Such a supersensitive CCD camera is preferably used because it is also capable of detecting slight intensity change in such weak chlorophyll fluorescence.

If a plant body is irradiated with excitation light of weak intensity (in a case where photosynthetic photon flux density (PPFD) is about 10 μmol $m^{-2}s^{-1}$), intensity of chlorophyll fluorescence excited by such excitation light is extremely weak. The supersensitive CCD camera is capable of reliably measuring such weak chlorophyll fluorescence.

An interval for measuring chlorophyll fluorescence, more specifically, temporal resolution for measurement of chlorophyll fluorescence intensity (intensity measurement interval) is not particularly limited as long as such temporal resolution enables formation of a time course curve of chlorophyll fluorescence intensity to be described later and determination of a maximum point and a minimum point on the time course curve.

Measurement of chlorophyll fluorescence by means of images every 0.06 seconds enables determination of a maximum point p of largest chlorophyll fluorescence intensity, a first minimum point s after the maximum point p, and a first maximum point m after the minimum point s as well as calculation of a P/S value and an M/S value, which are to be described later.

(Description of Analysis Means)

The analysis means is capable of diagnosing a health state of a plant from chlorophyll fluorescence measured by the fluorescence measurement means. The analysis means receives data of chlorophyll fluorescence measured by the light receiver by way of a cable, a wireless communication device, or the like. The analysis means includes an analyzer that is capable of analyzing the measurement data of chlorophyll fluorescence thus received.

(Description of Analyzer)

The analyzer is not particularly limited as long as it is capable of receiving measurement data of chlorophyll fluorescence transmitted from the light receiver and calculating chlorophyll fluorescence intensity from this measurement data.

When the light receiver is a CCD camera, chlorophyll fluorescence is measured by means of image data. In this case, the analyzer preferably includes an analysis program or the like for calculating chlorophyll fluorescence intensity at each site from this image data.

When the light receiver measures chlorophyll fluorescence by means of an image, if the analyzer calculates chlorophyll fluorescence intensity for each pixel configuring the image of chlorophyll fluorescence thus measured (hereinafter, referred to as chlorophyll fluorescence intensity image) and analyzes time course of the calculated chlorophyll fluorescence intensity, it is possible to obtain biological information of a plant body in an extremely small region of a pixel level. In this case, a health state of a plant individual body can be evaluated in more detail.

A plant has microlevel chlorophyll molecules. In measurement of a plant individual body, there are a large number of chlorophyll molecules in a plant body region corresponding to a pixel configuring an image captured by the CCD camera. It is thus possible to obtain chlorophyll fluorescence intensity enough to find a health state of a plant body even by calculating the chlorophyll fluorescence intensity from chlorophyll fluorescence of a pixel level.

If an inappropriate value is obtained by calculation of chlorophyll fluorescence intensity for each pixel due to noise or the like, it is possible to alternatively calculate average chlorophyll fluorescence intensity of a plurality of pixels (average chlorophyll fluorescence intensity of 25 pixels in a five pixel square).

In this case, in comparison to diagnosis in accordance with chlorophyll fluorescence intensity for each pixel, analysis speed increases and a signal/noise ratio (S/N ratio) increases, while spatial resolution deteriorates. Enabled therefore is easy and quick plant diagnosis of high reliability. The method mentioned above is significantly effective for finding health states of a large number of plant bodies in a large facility for cultivation of a huge number of plant individual bodies, for example.

The analyzer has a function of plotting chlorophyll fluorescence intensity calculated as described above in chronological order of measurement time and forming a time course curve of the chlorophyll fluorescence intensity. This time course curve is referred to as an induction curve, which is to be described in detail later.

The analyzer also has a function of determining a maximum point p of largest chlorophyll fluorescence intensity, a first minimum point s after this maximum point p, and a first maximum point m after this minimum point s in this induction curve, to calculate chlorophyll fluorescence intensity values (P, S, and M) at these extreme points. The analyzer further has a function of calculating a P/S value and/or an M/S value from the chlorophyll fluorescence intensity values (P, S, and M).

In the plant diagnostic device according to the present embodiment configured as described above, the light receiver in the fluorescence measurement means is capable of measuring chlorophyll fluorescence emitted by a plant individual body, and the analyzer in the analysis means is capable of forming an induction curve for a measurement site from the chlorophyll fluorescence thus measured. Furthermore, in accordance with this induction curve, the plant diagnostic device is capable of calculating a P/S value and/or an M/S value each obtained by comparison between the chlorophyll fluorescence intensity values (P, S, and M).

It is thus possible to diagnose a health state of the plant individual body in accordance with the P/S value and/or the M/S value at each site (such as each leaf, a distal end of a leaf, or a proximal end of a leaf) for which the induction curve has been formed. In other words, use of parameters such as P/S and M/S enables evaluation of a state of a photosynthetic function at each site in the plant individual body. In accordance with the P/S value and/or the M/S value, (1) it is possible to distinguish between plant bodies of different breeds, (2) it is possible to distinguish between different sites (a leaf portion and a stem portion, for example) in a plant individual body, and (3) it is possible to find disorder due to pests.

(1) Breed Discrimination

It is possible to reliably distinguish tomatoes A and B of different breeds having similar shapes in accordance with M/S values and P/S values calculated after measurement of the respective tomatoes. A state of a plant of each breed can be evaluated even in a case where plants of different breeds are cultivated in one field.

(2) Site Discrimination

In an identical plant individual body, a leaf portion and a stem portion have photosynthetic functions slightly different from each other. It is, however, possible to distinguish between the leaf portion and the stem portion in accordance with M/S values and P/S values calculated after measurement of the identical plant individual body. It is then possible to measure thickness of the stem portion (stem diameter) of each plant individual body. The thickness of a stem (stem diameter) in a plant is an important index for diagnosis of a plant growth state because an unhealthy plant individual body has a stem diameter smaller than that of a healthy plant individual body. It is thus possible to evaluate the health state of the plant by finding the stem diameter in accordance with the M/S value and the P/S value.

(3) Detection of Disorder Due to Pests

In accordance with P/S values calculated for respective leaves of a plant individual body, it is possible to detect a leaf or a portion of a leaf having a P/S calculation value smaller than those of the other leaves. Such a leaf or a portion of a leaf having a smaller P/S calculation value has a photosynthetic function poorer than those of the other healthy leaves, which suggests physiological disorder. It is therefore possible to detect some disorder in the leaf or the portion of the leaf (e.g. a leaf having a smaller P/S value carries pests or the like). In other words, it is possible to find overall damage status due to pests or the like in a plant individual body by comparing the P/S calculation values.

Meanwhile, in a leaf visually recognized as being uniformly healthy, it is possible to detect a site having an M/S calculation value smaller than those of the other sites in accordance with the M/S calculation values for this leaf. Such a smaller M/S calculation value for this site indicates a photosynthetic function poorer than those of the other healthy sites in the plant body or than the plant individual body. It is thus possible to detect some disorder even in such a leaf that seems to be healthy (e.g. a site having a smaller M/S value carries pests or the like on the rear surface of the leaf). In other words, it is possible to evaluate (diagnose) state variation in a plant individual body, which is hard to find by visual observation, by comparing the M/S calculation values.

In addition, the M/S values enable detection of smaller variation in photosynthetic function in comparison to the case of using the P/S values. It is thus possible to detect and diagnose pests or the like on a plant individual body in an early stage as well as a state of disorder progressed to some degree.

(Description of Method of Determining P, S, and M)

As described earlier, the device according to the present invention diagnoses a health state of a plant in accordance with the chlorophyll fluorescence intensity value P, the chlorophyll fluorescence intensity value S, and the chlorophyll fluorescence intensity value M (hereinafter, simply referred to as P, S, and M, respectively) in accordance with the induction curve. Specifically described below is how to determine the P, S, and M, which are used for diagnosis of the health state of the plant.

Figure 1:
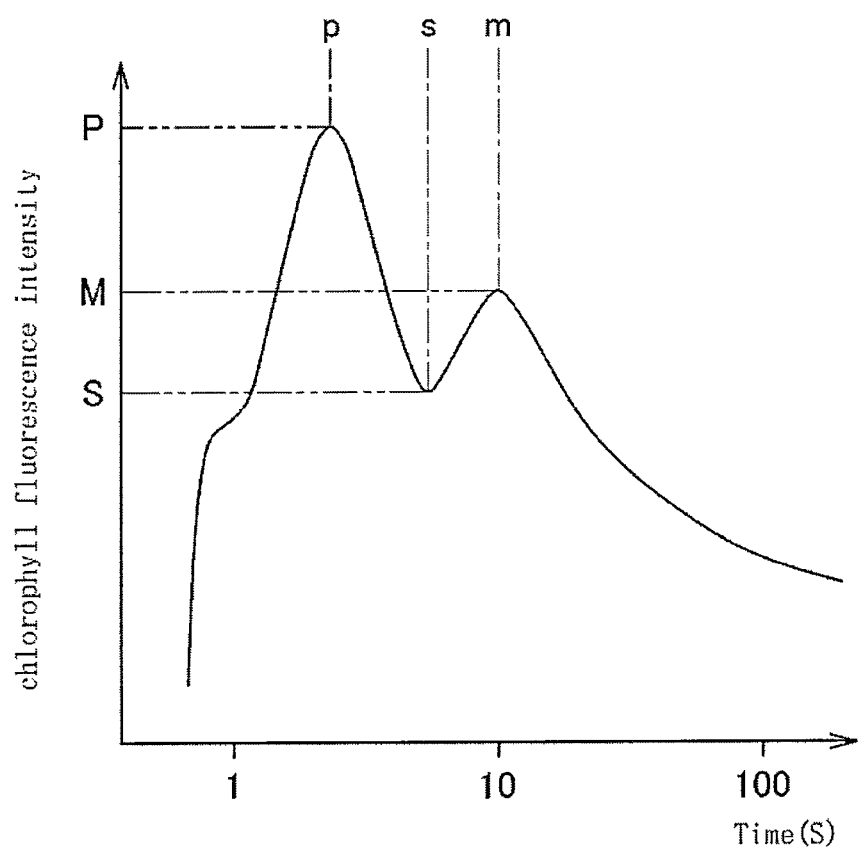
FIG. 1 is a conceptual graph of a time course curve of chlorophyll fluorescence intensity after irradiating a plant body with light.

As mentioned earlier, an induction curve is a time course curve that is formed by plotting chlorophyll fluorescence intensity in chronological order of measurement time. This time course curve has pluralities of peaks and bottoms. As shown in FIG. 1, an induction curve formed by measurement of a healthy plant body has at least two peaks. Out of these two peaks on the induction curve, the top of the largest peak (peak top) is denoted by a maximum point p, the top of the second largest peak (peak top) after the largest peak is denoted by a maximum point m, and a bottom connecting these two peaks is denoted by a minimum point s. At the maximum point p, the minimum point s, and the maximum point m, the maximum point p has the chlorophyll fluorescence intensity value P, the minimum point s has the chlorophyll fluorescence intensity value S, and the maximum point m has the chlorophyll fluorescence intensity value M, respectively.

The method of calculating the peak tops and the bottom is not particularly limited as long as it is capable of determining the two peak tops and the bottom between the two peaks. It is possible to adopt the following method, for example.

In general, chlorophyll fluorescence intensity occasionally includes noise. On a time course curve smoothed by noise reduction (time course curve obtained by smoothing), peak tops can be denoted by the maximum point p and the maximum point m, and the point having the minimum value between the two peaks can be denoted by the minimum point s. This smoothing can be achieved in various manners. The smoothing can be performed in accordance with the moving average method, the Fourier transform method, the Savitzky-Golay method, or the like. The smoothing is not limited to the above, but can be performed in accordance with any method as long as such a method achieves smoothing by noise reduction.

Alternatively, on an induction curve formed from raw data of measured chlorophyll fluorescence intensity, the points having maximum values at the respective peaks can be denoted by the maximum point p and the maximum point m, and the point having the minimum value between the two peaks can be denoted by the minimum point s.

Still alternatively, an average value of a plurality of chlorophyll fluorescence intensity values near each peak top can be denoted by the maximum point p or m, and an average value of a plurality of chlorophyll fluorescence intensity values near the bottom between the two peaks can be denoted by the minimum point s.

(Description of Method of Specifying Appearance Time Points for Maximum Point p, Minimum Point s, and Maximum Point m, in Unhealthy Plant Body)

In general, an induction curve obtained by the fluorescence measurement means and the analysis means varies in accordance with a breed, a season, a cropping type (a period from planting), a latest climate, and the like. The P/S value or the M/S value calculated in accordance with the induction curve varies accordingly.

It is thus necessary to define a P/S value or an M/S value of a healthy plant individual body as a diagnosis standard in order to diagnose a health state of a plant. More specifically, a large number of plant individual bodies and/or sites in a plant individual body are measured to obtain an average value of P/S values or M/S values and/or distribution from chlorophyll fluorescence thus measured. The value thus obtained can be set as a value of a standard healthy plant individual body and/or a standard healthy site of a plant body (hereinafter, referred to as reference value).

It is possible to cultivate a generally healthy plant body under a cultivation condition appropriately controlled throughout a year. Chlorophyll fluorescence of this healthy plant body having grown up is measured to form an induction curve in accordance with the chlorophyll fluorescence obtained by the measurement. This induction curve can be similar to that shown in FIG. 1, and thus it is possible to easily specify appearance time points for P, S, and M. The P/S value or the M/S value can be calculated from these P, S, and M. It is thus possible to diagnose the health state of the plant by comparison with the reference value.

Even among plants cultivated in a same cultivation environment, some of plant bodies in the plant cluster can be unhealthier than the other healthy plant bodies depending on a measurement period. On an induction curve formed in accordance with chlorophyll fluorescence obtained from such an unhealthy plant body, it can be difficult in some cases to specify appearance time points for P, S, and M in accordance with the induction curve. It is then difficult to calculate a P/S value or an M/S value, thereby failing to diagnose the health state of the plant by comparison with the reference value.

In accordance with the following method, it is possible to specify the appearance time points for P, S, and M on the induction curve formed by measurement of chlorophyll fluorescence of such an unhealthy plant.

(Specifying Method in Accordance with Induction Curve for Healthy Site in Plant Individual Body)

It is possible to form an induction curve for each pixel by measurement of chlorophyll fluorescence by means of an image. The shape of this induction curve can be analyzed at the pixel level. It is thus possible to form an induction curve for a healthy site and an induction curve for an unhealthy site in an identical plant individual body from an identical image. Appearance time points for P, 5, and M on the induction curve for the unhealthy site can be specified in accordance with the induction curve for the healthy site.

(Specifying Method in Accordance with Induction Curve for Healthy Plant Body Before or after Measurement Period)

If the number of measurement targets is small in a certain measurement period, appearance time points for P, S, and M cannot be specified in some cases in accordance with an induction curve formed for the measurement period. In such a measurement period (hereinafter, referred to as unmeasurable period), the appearance time points for P, S, and M can be specified on the induction curve for the plant body in the unmeasurable period in accordance with an induction curve for a healthy plant body formed before or after the unmeasurable period. For example, the appearance time points for P, S, and M can be specified on the induction curve for the plant body in the unmeasurable period in accordance with an induction curve for a healthy plant body formed several days before or several weeks after the unmeasurable period in an identical individual body cluster or in an identical individual body.

Furthermore, in an identical individual body cluster or in an identical individual body, due to difference in growth degree of the plant bodies, for example, between a growing plant body and a fruiting plant body, it is impossible in some cases to apply the appearance time points for P, S, and M in accordance with the induction curve for the past or future healthy plant body. Even in such a case, the appearance time points for P, S, and M can be specified on the induction curve for the plant body in the unmeasurable period in accordance with an induction curve formed previously for a healthy plant body of similar growth degree. For example, if year 2011 has an unmeasurable period, appearance time points for P, S, and M can be specified on an induction curve for a plant body in the unmeasurable period in accordance with an induction curve formed in a measurement period for a healthy plant body of similar growth degree in year 2010.

Furthermore, it is impossible in some cases to apply the appearance time points for P, S, and M specified in accordance with the induction curve for the healthy plant body formed with use of the past plant body in the unmeasurable period. For example, there is a case where a cultivation environment in the unmeasurable period has a climate much hotter than the average year. In such a case, the appearance time points for P, S, and M can be specified on the induction curve for the plant body in the unmeasurable period in accordance with an induction curve formed for a past healthy plant body cultivated in a cultivation environment similar to that in the unmeasurable period.

(Methods of Specifying Arbitrary Appearance Time Points)

In a case where appearance time points for P, S, and M cannot be specified in accordance with any of the methods described above, it is possible to set appearance time points for P, S, and M in accordance with an induction curve for a healthy plant body of a breed similar to a cultivated plant. It is also possible to artificially set appearance time points for P, S, and M in accordance with an empirical rule or the like as necessary. In a case of irradiating a plant body with excitation light, it is possible to set a chlorophyll fluorescence intensity value between the start of irradiation and 0.1 to 10 seconds as P, a chlorophyll fluorescence intensity value between the appearance time point for P and 0.1 to 10 seconds as S, and a chlorophyll fluorescence intensity value between the appearance time point for S and 0.1 to 20 seconds as M, respectively.

The methods for calculating the values are also applicable to a case of extracting, from sites of a plant body to be target regions in measurement of one time by means of an image, a site having a photosynthetic function poorer than the other sites due to pests or the like (damage to a crop due to pathogenic bacteria or pests).

(Description of P/S Value)

The analyzer can have a function of calculating chlorophyll fluorescence intensity values (P, S, and M) at the extreme points in an induction curve and calculating a P/S value obtained by comparing between the chlorophyll fluorescence intensity values (P and S) in accordance with the chlorophyll fluorescence intensity values (P and S) out of these chlorophyll fluorescence intensity values.

In this case, in accordance with the P/S value, it is possible to discriminate between a leaf portion and a stem portion in a plant individual body, detect photosynthesis malfunction due to water stress, and detect disease and insect damage having progressed relatively.

In the case where chlorophyll fluorescence of a plant is measured by means of an image or the like, it is possible to measure a stem diameter of the plant individual body in accordance with distribution of P/S values. It is thus possible to evaluate growth degree of the plant individual body.

More specifically, it is possible to reliably find a stem portion of the plant individual body from the maximum point p that can be reliably determined on an induction curve. It is thus possible to find a growth state of the plant individual body and apply appropriate treatment to the plant individual body.

For example, a plant individual body of poor growth can have a stem diameter smaller than that of a healthy plant individual body. It is thus possible to provide the plant individual body with additional fertilizer.

More specifically, in comparison to an induction curve for a healthy plant individual body, an induction curve for the plant individual body of poor growth has a shape including almost same chlorophyll fluorescence intensity values (P and M) at the maximum point p and the first maximum point m after the minimum point s but a slightly larger chlorophyll fluorescence intensity value (S) at the first minimum point s after the maximum point p. Even in such a case where the chlorophyll fluorescence intensity value (S) is different slightly, it is possible to reliably measure the stem diameter of the plant individual body by calculation of a P/S value. In other words, the P/S value is calculated in accordance with a smaller decreasing rate from the chlorophyll fluorescence intensity value (P) to the chlorophyll fluorescence intensity value (S) as well as by setting, as a denominator, the smallest chlorophyll fluorescence intensity value (S) out of the chlorophyll fluorescence intensity values (P, S, and M). In this case, the smaller chlorophyll fluorescence intensity value (S) is set as the denominator in comparison to a calculation method in which the chlorophyll fluorescence intensity value (P) is set as a numerator and an average value between the chlorophyll fluorescence intensity value (S) and the chlorophyll fluorescence intensity value (M) is set as a denominator. Use of the P/S value enables more reliable and sensitive numerical evaluation of poor growth, in other words, deterioration in health state, of the plant individual body.

For example, chlorophyll fluorescence of a plant body is measured as image data. The analyzer calculates P/S values from the image data thus measured. An image formation unit forms a P/S image of the plant body in accordance with the P/S values. In this case, a leaf portion of the plant body has a P/S calculation value larger than that for a stem portion of the plant body. It is possible to extract an image of the stem portion from the P/S image of the plant body by adjustment in color of the P/S image in accordance with the P/S value for the leaf portion and the P/S value for the stem portion. It is thus possible to measure thickness (stem diameter) of a stem from the extracted stem portion.

Accordingly, it is possible to cultivate plants in stable growth states as an entire plant cluster in a plant production field, with a result of stabilization in quality and crop yield of products such as fruits.

(Description of Case of Simultaneously Using M/S Value and P/S Value)

The analyzer can have a function of calculating both an M/S value and a P/S value. In this case, it is possible to simultaneously both the M/S value and the P/S value in an identical measurement period. More specifically, it is possible to simultaneously use two parameters of M/S and P/S in measurement of one time. A health state of a plant individual body can be thus diagnosed more accurately.

For example, as to be described later, it is possible to simultaneously form an M/S image and a P/S image by measuring chlorophyll fluorescence of a plant body as image data. With use of the P/S image, it is possible to detect a leaf damaged by pests (such as tomato russet mite) in a plant individual body. It is thus possible to find overall damage status due to pests or the like in the plant individual body with use of the P/S image. With use of the M/S image, it is possible to detect disorder due to pests in an initial stage, which is difficult to be visually recognized, on a leaf of the plant individual body. More specifically, with use of the M/S image, it is possible to detect even a leaf having disorder due to pests in an initial stage in the plant individual body, while such a leaf is difficult to be detected in the P/S image. The M/S image thus realizes estimation of progress speed of disorder due to pests in the plant individual body.

Accordingly, each of the M/S value and the P/S value is numerical information obtained from functional information of an identical photosynthetic reaction system. It is possible to obtain pieces of information highly relevant to health of the plant by simultaneously using the parameters of M/S and P/S, thereby achieving detailed plant diagnosis.

In order to find a health state of a plant individual body to some extent, the analyzer can have a function of calculating only a P/S value without a function of calculating an M/S value.

(Description of Long Wavelength Transmissive Member)

The fluorescence measurement means preferably includes a long wavelength transmissive member that is attached to the light receiver and selectively allows transmission of only chlorophyll fluorescence.

In this case, only chlorophyll fluorescence is selectively transmissive so that the light receiver (such as a CCD camera) measures only the chlorophyll fluorescence. Examples of the long wavelength transmissive member include an optical filter (such as a long pass filter) that allows transmission of light of 680 nm or longer. This long pass filter advantageously allows selective transmission of chlorophyll fluorescence that has maximum emission intensity of a wavelength longer than 683 nm.

In a case where the light receiver has sensitivity in an infrared region (such as a CCD camera that is capable of measuring an infrared region), it is possible to advantageously realize sensitive measurement of chlorophyll fluorescence having maximum emission intensity of a wavelength longer than 683 nm.

(Description of Irradiation Means)

As shown in FIG. 2, the plant diagnostic device according to the present embodiment can include irradiation means for irradiating a plant body with excitation light that is capable of exciting chlorophyll.

The irradiation means thus provided is capable of irradiating a plant body with excitation light at desired timing upon measurement of chlorophyll fluorescence. The chlorophyll fluorescence can be released to a leaf portion at desired timing.

It takes only an extremely short period of time of less than 0.01 seconds for chlorophyll to emit chlorophyll fluorescence after coming into an excited state. If the irradiation means and the fluorescence measurement means operate in cooperation with each other by control means to be described later, it is possible to reliably measure chlorophyll fluorescence emitted by irradiation with excitation light from the emission start time point. The plant diagnostic device according to the present embodiment preferably includes the control means for controlling the fluorescence measurement means and the irradiation means, in order to realize accurate measurement of chlorophyll fluorescence emitted by chlorophyll (see FIG. 2).

(Exemplification of Control Means)

The control means mentioned above is not particularly limited in terms of its function and the like, but can have a function of transmitting to the irradiation means a signal for commanding start of irradiation with excitation light and simultaneously transmitting to the fluorescence measurement means a signal for commanding start of measurement of chlorophyll fluorescence. The control means is capable of controlling the fluorescence measurement means and the irradiation means so as to operate in cooperation with each other. The fluorescence measurement means is thus capable of reliably measuring emission of chlorophyll fluorescence from the start of emission.

The control means preferably transmits a signal indicating that the fluorescence measurement means starts measurement of chlorophyll fluorescence also to a storage unit of the analyzer to be described later, so that the storage unit stores reception time of the signal or the like, because it is possible to find measurement start time when the analyzer calculates a time course curve of chlorophyll fluorescence intensity.

(Description of Light Source)

A light source of the irradiation means is not particularly limited as long as it is capable of exciting chlorophyll. For example, the light source is preferably a blue LED that is capable of irradiating a plant with blue light having maximum emission intensity around 450 nm, because, upon measurement of chlorophyll fluorescence, it is possible to relatively easily distinguish between reflected light of this blue excitation light and the chlorophyll fluorescence having maximum emission intensity of a wavelength longer than 683 nm. It is possible to reliably measure only the chlorophyll fluorescence by provision of the long wavelength transmissive member, because the long wavelength transmissive member cuts the reflected light of the blue excitation light.

The irradiation means is preferably disposed at a distal end of a plant individual body in an extending direction (perpendicular to the ground surface), so as to irradiate, with excitation light, a site around a growth point of a stem tip in the plant individual body. The site around the growth point of the plant is formed while being influenced by a nearest environment condition and the health state of the plant individual body, and thus tends to reflect the health state of the plant individual body.

For example, the light source is disposed to be substantially parallel to the extending direction as well as to be opposite to the site around the growth point of the stem tip, so that the site around the growth point of the stem tip in the plant individual body can be irradiated with excitation light. In this state, excitation light emitted from the light source can be applied to the site around the growth point of the step tip of the plant. More specifically, when the irradiation means is a planar panel light source that includes a plurality of blue LEDs in an identical plane, it is possible to irradiate the site around the growth point of the stem tip in the plant with excitation light widely and as substantially uniformly as possible.

The light source disposed so as to be substantially parallel to the extending direction of a plant preferably has a hoist mechanism that is shiftable upward and downward. In this case, the light source being hoisted is capable of irradiating, with excitation light, not only the site around the growth point of the stem tip in the plant but also the entire plant individual body.

(Description of Storage Unit)

The analysis means is preferably provided with the storage unit that is capable of storing measured chlorophyll fluorescence. Examples of the storage unit can be a hard disk that is capable of storing data of chlorophyll fluorescence measured for each plant individual body. In this case, it is possible to reanalyze or referred to the chlorophyll fluorescence data as necessary, which is basic data for diagnosis of a state of a plant.

(Description of Image Formation Unit)

In the case where a CCD camera or the like measures chlorophyll fluorescence as image data, preferably, the analysis means calculates an M/S value and/or a P/S value for each pixel configuring the image, and includes the image formation unit that forms a chlorophyll fluorescence parameter image (hereinafter, referred to as an M/S image or a P/S image) obtained with use of the M/S values and/or the P/S values thus calculated.

In this case, with use of the M/S image, it is possible to find a state of a plant individual body that cannot be visually recognized from outer appearance. With use of the P/S image, it is possible to find growth degree of a plant individual body as well as a state of the plant individual body.

As described earlier, each of the P/S value and the M/S value is numerical information that is obtained from functional information of the identical photosynthetic reaction system. Slight change in state of a plant obtained from the P/S value and the M/S value is highly relevant to health of the plant. In other words, even in a case where the P/S value is used for diagnosis of a health state of a plant in place of the M/S value, it is possible to diagnose similarly to diagnosis of the health state of the plant in accordance with the M/S value.

Representatively described below is a case of diagnosing a health state of a plant in accordance with the M/S value, out of the P/S value and the M/S value.

More specifically, it is impossible to visually distinguish from outer appearance between a leaf of a plant individual body in an initial stage of disease and insect damage and a leaf with no disease and insect damage. Such disease and insect damage cannot be detected unless carefully checking each of the leaves (see FIG. 4(A)).

In a case where the image formation unit is provided with a display or the like for displaying an M/S image, a site damaged by pests is displayed to have an M/S value smaller than a healthy site. It is thus possible to recognize distribution of sites having disorder due to disease and insect damage in the plant body on the display. In other words, it is possible to detect, with use of the M/S image, disease and insect damage, which cannot be detected by directly visually checking leaves (see FIG. 4(B)).

It is thus possible to easily specify a site having disease and insect damage, as well as find disorder in an initial stage, as to be described later. Such disease and insect damage can be removed in an early stage by spraying just a small amount of an agricultural chemical only to the site having disease and insect damage.

Figure 4:
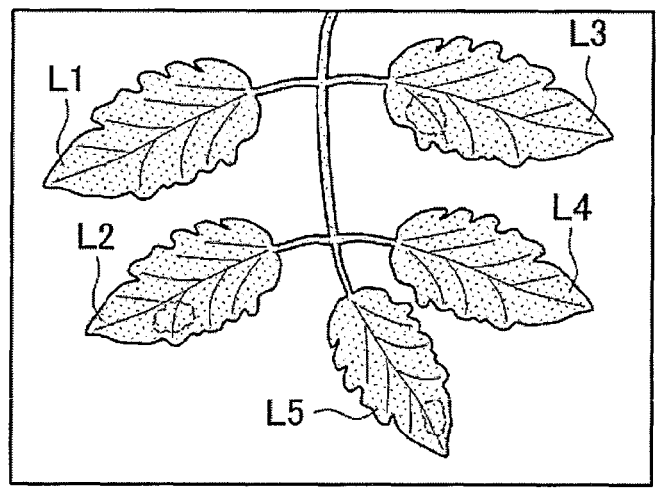
Figure 4:
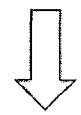
Figure 4:
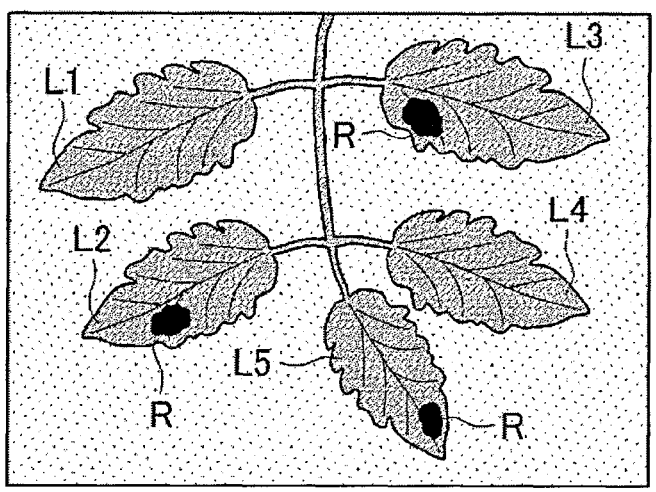

For example, as shown in FIG. 4(A), even when the leaves of the plant partially (in portions surrounded by dotted lines in FIG. 4(A)) have disease and insect damage, its influence does not appear as visually recognizable disorder (hereinafter, referred to as visible disorder) in an initial stage. It is thus impossible to visually distinguish between leaves having disease and insect damage in the initial stage and healthy leaves. It is more difficult to detect by visual observation if a leaf carries pests on the rear surface.

On the other hand, as shown in FIG. 4(B), with use of the M/S image of the leaves of the plant, out of the leaves visually recognized as in substantially same states, portions having disorder in an initial stage due to disease and insect damage (portions surrounded by the dotted lines in FIG. 4(A)) on a leaf (L2), a leaf (L3), and a leaf (L5) are detected as states different from the other portions (black portions R shown in FIG. 4(B)). The disease and insect damage can be thus detected in the initial stage.

The image formation unit can change colors of respective pixels in the image in accordance with the M/S values. For example, with an M/S value for a healthy site being set as a reference value, the M/S values for the respective sites can have different colors and the like as the M/S values decrease (as to be described later, the M/S value decreases depending on degree of disorder). It is then possible to easily discriminate between a healthy site and a damaged site on the display or the like. In addition, a level of disorder can be discriminated by means of its color, which is preferred because it is possible to easily determine whether or not the site has disorder in an initial stage.

Described next is a method of diagnosing a health state of a plant body by the analyzer of the plant diagnostic device described above.

The analyzer diagnoses a health state of a plant in accordance with chlorophyll fluorescence measured by the light receiver.

More specifically, in accordance with an M/S value obtained by comparison between the chlorophyll fluorescence intensity values (S and M) calculated from a time course curve (induction curve) of chlorophyll fluorescence intensity, a physiological function (more particularly, a photosynthetic function) of the plant, which cannot be visually recognized from outer appearance, is numerically evaluated. It is then possible to detect change in health state of the plant individual body in an early stage.

More particularly, the time course curve (induction curve) of chlorophyll fluorescence intensity changes in shape in accordance with the state of the photosynthetic function. The method according to the present invention enables accurate numerical conversion of even slight change and thus realizes accurate diagnosis of the state of the plant individual body.

Furthermore, the analyzer is capable of numerically evaluating the physiological function (more particularly, the photosynthetic function) of the plant individual body in accordance with a P/S value obtained by comparison between the chlorophyll fluorescence intensity values (P and S) calculated from the time course curve (induction curve) of chlorophyll fluorescence intensity. In the case where chlorophyll fluorescence of the plant is measured by means of an image or the like, it is possible to measure a stem diameter of the plant individual body in accordance with distribution of P/S values from the P/S image. It is thus possible to evaluate growth degree of the plant individual body. Accordingly, it is possible to produce plants of stable sizes as an entire plant cluster in a plant production field, with a result of stabilization in crop yield of fruits or the like.

When the analyzer calculates a P/S value, with a P/S value for a healthy plant body or a healthy site in a plant body being set as a reference value, it is possible to diagnose whether or not the plant has disorder due to pests.

As described above, even in a case where the P/S value is used for diagnosis of a health state of a plant in place of the M/S value, it is possible to diagnose similarly to diagnosis of the health state of the plant in accordance with the M/S value.

Representatively described in detail below is the M/S value out of the P/S value and the M/S value.

As described earlier, data of chlorophyll fluorescence measured by the light receiver (such as chlorophyll fluorescence image data measured by a CCD camera) is transmitted to the analysis means. The analyzer included in the analysis means executes the following processing in accordance with the chlorophyll fluorescence data thus received.

Upon receipt of chlorophyll fluorescence measured by the light receiver, the analyzer calculates chlorophyll fluorescence intensity from the chlorophyll fluorescence thus received. The calculated chlorophyll fluorescence intensity values are plotted along a time axis so as to correspond to measurement time of the chlorophyll fluorescence by the light receiver, and there is formed a time course curve (induction curve) of the chlorophyll fluorescence intensity (see FIG. 1).

When the induction curve is formed, the analyzer determines a maximum point p of largest chlorophyll fluorescence intensity, a first minimum point s after this maximum point p, and a first maximum point m after this minimum point s, as characteristic extreme points in this induction curve, to calculate chlorophyll fluorescence intensity values (P, S, and M) at these extreme points.

Out of these extreme points, in accordance with the chlorophyll fluorescence intensity values (M and S) at the maximum point m and the minimum point s, the chlorophyll fluorescence intensity value S and the chlorophyll fluorescence intensity value M are compared with each other. More particularly, an M/S value is calculated by dividing the chlorophyll fluorescence intensity value M by the chlorophyll fluorescence intensity value S.

It is then possible to evaluate the health state of the plant in accordance with the M/S value thus calculated.

More specifically, in a case of a leaf of a plant, it is possible to discriminate between a damaged site and a healthy site in accordance with distribution of calculated M/S values for an individual leaf surface.

Described below is a principle on the basis of which a damaged site and a healthy site can be discriminated from each other in accordance with M/S values.

When a leaf of a plant has pests (such as tomato russet mite as one type of rust mites), such pests damage the leaf directly or indirectly (for example, by means of a secretion discharged from the pests). The pests themselves are extremely smaller than the plant body, but certainly cause disorder in a photosynthetic organ. Examples of such disorder include inhibition of an electron transport system in photosynthetic reaction. Inhibition of the electron transport system in the photosynthetic reaction system causes deterioration in function such as generation of NADPH and generation of ATP driven by $H^+$ gradient inside and outside a thylakoid membrane, at and after a photochemical system I (PSI) in the photosynthetic reaction conducted in cooperation therewith. In other words, deterioration in function of the initial reaction system in the photosynthetic reaction influences and causes deterioration in function of the subsequent reaction systems.

An induction curve formed by the analyzer is known as corresponding to photosynthetic reaction conducted in a plant. For example, a course from the maximum point p of the largest chlorophyll fluorescence intensity value to the first minimum point s after the maximum point p is mainly influenced by activation of photosynthetic electron transport. A course from the first maximum point m after the minimum point s reflects not only the activation of photosynthetic electron transport but also the generation of a high energy level through the thylakoid membrane, activation of the photosynthetic reaction system, and the like.

In the induction curve calculated from chlorophyll fluorescence at a site having disorder due to disease and insect damage, the shape from the maximum point p of the largest chlorophyll fluorescence intensity value largely changes in comparison to an induction curve for a healthy site, because of deterioration in function of the photosynthetic reaction system, as described above.

Figure 3:
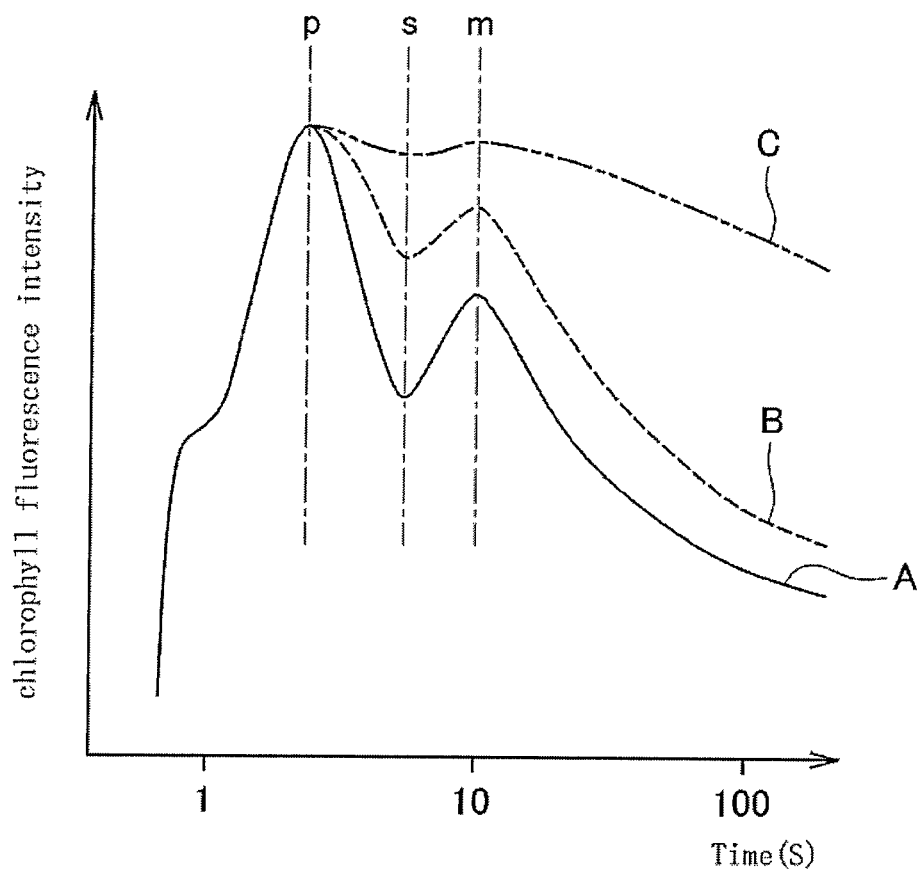
FIG. 3 is a conceptual graph of time course curves of chlorophyll fluorescence intensity after irradiating a plant body with light, in which (A) is a conceptual graph of a time course curve for a healthy site, (B) is a conceptual graph of a time course curve for a site having physiological functional disorder such as decrease in amount of chlorophyll or activation of a heat dissipation path, and (C) is a conceptual graph of a time course curve for a site having a photosynthesis photochemical reaction system inhibited by disorder.

Such change is described with reference to FIG. 3. FIG. 3 is a conceptual graph of induction curves (a curve A, a curve B, and a curve C in FIG. 3) for a healthy site, a site having initial disorder (hereinafter, simply referred to as initially disordered site), and a site having a photosynthetic function remarkably deteriorated by disorder (hereinafter, referred to as terminally disordered site), respectively.

In order to emphasize differences in shape thereamong, these curves are normalized (corrected so as to have equal p values) with use of the chlorophyll fluorescence intensity values P at the maximum points p of the largest chlorophyll fluorescence intensity values on the curves.

As indicated by the curve A in FIG. 3, the induction curve for the healthy site has the first minimum point s after the maximum point p of the largest chlorophyll fluorescence intensity and the first maximum point m after the minimum point s, which are recognized easily.

As indicated by the curve B in FIG. 3, however, the leaf having pests in the initial stage has slight damage to the photosynthetic reaction system as described above, and thus functions properly to some extent. The chlorophyll fluorescence intensity values (S and M) at the first minimum point s after the maximum point p and the first maximum point m after the minimum point s are larger than those for the healthy site. It is because light energy, which is to be used by activation of the photosynthetic reaction system in a healthy state, is emitted as chlorophyll fluorescence due to deterioration in function of the photosynthetic reaction system.

As indicated by the curve C in FIG. 3, when disease and insect damage progresses and the photosynthetic function remarkably deteriorates, it is hard to recognize the first minimum point s after the maximum point p and the first maximum point m after the minimum point s.

By determining these characteristic extreme points, namely, the first minimum point s after the maximum point p and the first maximum point m after the minimum point s and using the chlorophyll fluorescence intensity values (S and M) at these extreme points, it is possible to numerically convert and evaluate the state of the photosynthetic function. For example, it is possible to detect the initially disordered site by disease and insect damage as indicated by the curve B in FIG. 3.

On the basis of the principle described earlier, when the analyzer calculates an M/S value, with the M/S value for a healthy site being set as a reference value (for example, an average value of all M/S values measured at many healthy sites on a leaf can be regarded as a value for a healthy site), it is possible to specify the initially disordered site that has initial disorder by disease and insect damage.

By comparing the induction curves for the site having a photosynthetic function initially disordered by pests or the like and for the healthy site, a clear difference is detected in the shapes of the curves from the maximum point p of the largest chlorophyll fluorescence intensity value. This characteristic difference in shape can be numerically converted as the M/S values. By the method according to the present invention, comparison between the M/S values enables detection of slight change in photosynthetic function.

If excitation light applied from outside the surface of the plant body has constant intensity, it is possible to evaluate the photosynthetic function by calculating the chlorophyll fluorescence intensity values (P, S, and M) on the induction curve comparing between the chlorophyll fluorescence intensity values (so-called absolute values) and finite differences, or the like.

Upon measurement of a plant individual body, the entire surface of the plant body is not irradiated with excitation light of constant intensity. It is possible to accurately evaluate the photosynthetic function in each site of the plant individual body in accordance with the M/S value obtained by comparison between the chlorophyll fluorescence intensity values (S and M) as in the present invention, regardless of the intensity of the applied excitation light.

(Description of Discrimination Method Between Leaf Portion and Stem Portion)

The method according to the present invention enables detection of even slight difference in photosynthetic function and thus enables detection of a difference in photosynthetic function due to different sites in a plant.

More specifically, in a plant, although a leaf portion as a main organ for conducting photosynthesis and a stem portion hardly functioning as a photosynthetic organ have photosynthetic functions largely different from each other, although the both portions are in green and contain chlorophyll. It is thus possible to discriminate between the leaf portion and the stem portion in the plant individual body.

For example, chlorophyll fluorescence of a plant body is measured as image data. The analyzer calculates M/S values from the image data thus measured. An image formation unit forms an M/S image of the plant body in accordance with the M/S values. In this case, a leaf portion of the plant body has an M/S calculation value larger than that for a stem portion of the plant body. It is possible to extract an image of the stem portion from the M/S image of the plant body by adjustment in color of the M/S image in accordance with the M/S value for the leaf portion and the M/S value for the stem portion. It is thus possible to measure thickness (stem diameter) of a stem from the extracted stem portion.

In the case where a leaf portion and a stem portion can be discriminated from each other in a plant individual body, it is possible to easily measure the size of the diameter of the stem portion (stem diameter) with use of image data, thereby realizing evaluation of a growth state of the plant. If the stem has a diameter not more than a predetermined reference value in the growth stage, the plant individual body can be provided with more fertilizer, for example. It is then possible to cultivate plants of stable sizes as an entire plant cluster in a plant cultivation field, with a preferred result of stabilization in quality and crop yield of products such as fruits.

(Others)

In a case where it is difficult to calculate the first minimum point s after the maximum point p of the largest chlorophyll fluorescence intensity and the first maximum point m after the minimum point s on the formed induction curve, calculation can be conducted with a first inflection point after the maximum point p being set as the minimum point s and a first inflection point after the minimum point s being set as the maximum point m, so as to obtain effects similar to the above.

Alternatively, upon plotting chlorophyll fluorescence intensity values in chronological order of measurement time, when adjacent plots are connected by straight lines after a time point of the largest chlorophyll fluorescence intensity value (in other words, the appearance time point for P in the induction curve), a first time point having minimum inclination can be set as the appearance time point for S. Furthermore, when adjacent plots are connected by straight lines after the point S, a first time point having minimum inclination can be set as the appearance time point for M. In this case, it is possible to specify the appearance time points for S an M in a case where the first minimum point after P and the first maximum point after this minimum point are difficult to be specified in a formed induction curve (in other words, the induction curve has a small difference between a peak and a bottom).

(Description of Noise Reduction)

The analyzer receives data of chlorophyll fluorescence measured by the light receiver, calculates chlorophyll fluorescence intensity from the measurement data of the chlorophyll fluorescence thus received, and forms an induction curve. If the chlorophyll fluorescence intensity calculated from the data of the chlorophyll fluorescence measured by the light receiver is small, the formed induction curve can have larger noise. In order to reduce such noise, it is preferred to utilize a moving average of fluorescence intensity upon output of chronological change in chlorophyll fluorescence intensity, and form an induction curve. Obtaining the moving average leads to noise reduction, with a result of more accurate determination of the extreme points and the inflection points.

(Diagnosis in Accordance with SPA Concept)

Use of the plant diagnostic device and the plant diagnostic method according to the present embodiment enables diagnosis of a health state of a plant individual body with use of a sensor such as a CCD camera for measuring chlorophyll fluorescence as biological information on the plant, with no damage or contact to the plant individual body. Without collecting a leaf or the like from a plant individual body, measuring chlorophyll concentration or the like in accordance with a chemical analysis method or the like, or measuring biological information of the plant individual body therefrom at the level of a laboratory, it is possible to realize a Speaking Plant Approach (SPA) in which a state of a plant is diagnosed with use of various sensors in accordance with biological information of the plant individual body with no damage or contact and the cultivation environment for the plant body is appropriately controlled in accordance with the diagnosis result.

The plant diagnostic device according to the present embodiment is capable of diagnosing states of plants more efficiently in a cultivation field where diagnosis of the growth states of the plants are essential, especially in large-scale cultivation, because there is no need to damage or contact plant individual bodies for the diagnosis of the states of the plants.

Example 1

Effectiveness of the plant diagnostic device and the plant diagnostic method according to the present invention was checked.

In tests, when each plant body in a dark condition was irradiated with excitation light for exciting chlorophyll from the light source, the light receiver measured chlorophyll fluorescence emitted by the chlorophyll so as to conduct evaluations (1) to (3) on the basis of the measurement data of chlorophyll fluorescence.

(1) Detection of a difference in photosynthetic function between different breeds (2) Detection of a difference in photosynthetic function between different sites in an identical individual body (3) Possibility of diagnosis in an early stage of disorder by pests The effectiveness of the device and the method according to the present invention were checked in these tests.

In the tests, the above evaluations were made on the basis of an average value of chlorophyll fluorescence obtained from a plurality of plant individual bodies.

The tests were conducted with use of devices under the condition as follows.

Used as the light source was a blue LED panel (manufactured by Senecom Corporation, model number: SE-LP60) that includes blue LEDs disposed at an interval of about 3 cm in a grid pattern on a plate member of about 65 cm wide and about 65 cm long. This blue LED panel was placed so as to be substantially parallel to the extending direction of a plant individual body as well as to be opposite to a site around a growth point of a stem tip, and the plant was irradiated with excitation light from a distance of about 60 cm from the site around the growth point of the stem tip.

The blue LEDs included in the blue LED panel, each radiate blue excitation light having largest intensity around 450 nm at about 25° C. (PPFD: about 15 to 200 $\mu molm^{-2}s^{-1}$: intensity of light applied to a plane at a distance of 30 to 60 cm from a light source surface).

Used as the light receiver was a CCD camera (manufactured by Allied Vision Technologies GmbH, model number: Stingray F145B ASG). This CCD camera was placed at a distance of about 60 cm from the site around the growth point of the stem tip, and measured was chlorophyll fluorescence that was excited by blue excitation light emitted from the light source.

The CCD camera was provided at a front surface of a lens with a long wavelength transmissive member (long pass filter (manufactured by FUJIFILM Corporation, model number: SC-66)) that allows selective transmission of chlorophyll fluorescence. This member is provided in order to prevent blue excitation light emitted from the light source from being partially measured by the CCD camera as reflected light.

The CCD camera had shutter speed of 0.06 seconds, and a frame rate of 15 images/second.

In order that analysis means to be described later more accurately calculates chlorophyll fluorescence intensity from luminance values of images of chlorophyll fluorescence measured by the CCD camera, checked was the relationship between luminance of the images measured by the CCD camera and light intensity. Confirmed as a result was that relationship therebetween has high linearity (in a range in which an average luminance value of measured images (256 gradations) is 0 to 220, $R^2=0.996$).

The tests were conducted at night while the plants were in a dark condition, in order to eliminate influence by sunlight.

The light source and the light receiver were controlled by the control means so as to operate in cooperation with each other. The control means had a program for transmitting a signal via cable to each of the blue LED panel, the CCD camera, and the analysis means to be described later. This program has a function of transmitting a signal to each of the following devices.

(I) To the blue LED panel, the program transmits an irradiation start signal for applying excitation light and transmits a signal for ending irradiation after about 100 seconds from the start.

(II) To the CCD camera, the program transmits a measurement start signal simultaneously with the irradiation start signal, and transmits a signal for setting the shutter speed to 0.06 seconds and the frame rate to 15 images/second.

(III) The program transmits image data of chlorophyll fluorescence thus measured to the analysis means to be described later.

Used as the analysis means was a note PC (manufactured by Lenovo Japan, model number: ThinkPad R61e).

This note PC had a hard disk (HD). This HD was used as the storage unit. This PC has a program that is capable of storing a plurality of pieces of image data of chlorophyll fluorescence for each plant individual body in the HD.

Also installed into this PC was a chlorophyll fluorescence image processing program that is capable of calculating chlorophyll fluorescence intensity and the like. This program was self-made with use of Visual Basic 6.0 (manufactured by Microsoft Corporation) and was used for analysis.

This chlorophyll fluorescence image processing program has the following functions.

(I) If a representative piece of image data is selected from pieces of image data of a plant individual body stored arbitrarily and independently in the HD and an analysis target region is specified in this selected image data, the program automatically calculates chlorophyll fluorescence intensity value in the region same as the region specified in the representative image, for each of the other pieces of image data, and calculates an average value of the chlorophyll fluorescence intensity values.

The program can alternatively have a function of extracting an image of the largest average luminance from the chlorophyll fluorescence image data and automatically determining a region of the plant body in this image in accordance with a predetermined threshold.

(II) The program forms an induction curve for the specified region.

(III) On the induction curve thus formed, the program calculates a maximum point p of the largest chlorophyll fluorescence intensity, the first minimum point s after the maximum point p, and the first maximum point m after the minimum point s (hereinafter, these extreme points are simply referred to as the maximum point p, the minimum point s, and the maximum point m, respectively), and calculates an M/S value or/and a P/S value from chlorophyll fluorescence intensity values (P, S, and M) at these extreme points.

(IV) The program forms an M/S image or/and a P/S image in accordance with the M/S value or/and the P/S value thus calculated.

Upon formation of the induction curve, noise reduction was conducted by the chlorophyll fluorescence image processing program.

If it was difficult to calculate the extreme points, namely, the maximum point p of the largest chlorophyll fluorescence intensity, the first minimum point s after the maximum point p, and the first maximum point m after the minimum point s on the formed induction curve, calculation was conducted with a first inflection point after the maximum point p being set as the minimum point s and a first inflection point after the minimum point s being set as the maximum point m.

In order to measure the plurality of plant individual bodies as described above upon the evaluations in the present invention, there was self-made a cart so that the device according to the present invention can be easily disposed at a predetermined position with respect to the plant individual bodies as the measurement targets. This cart is capable of moving on a rail that is provided on a floor surface so as to be parallel to a cultivation bed. This cart has a hoist member that is coupled to a seat of the cart and is capable of adjusting height in the vertical direction. The CCD camera and the blue LED panel were provided on the hoist member.

(1) Detection of a Difference in Photosynthetic Function Between Different Breeds Confirmed with use of two breeds of tomatoes (Tomimaru Mucho and Reika) was that it is possible to detect a slight difference in photosynthetic function between the different breeds in accordance with the M/S values and the P/S values calculated by the device according to the present invention.

In order to eliminate influence by variation in light intensity of excitation light applied to chlorophyll, each induction curve was normalized such that the largest chlorophyll fluorescence intensity value P at the maximum point p is equalized with 1. Hereinafter an induction curve normalized in this manner is referred to as a normalized induction curve.

(Comparison of Total Chlorophyll Content)

With use of twelve tomatoes (Tomimaru Mucho) and seven tomatoes (Reika), a total chlorophyll content (the method according to Porra et al. (1989)) in an unit area in a leaf was measured for each of these breeds. In this method, a leaf was corrected from each plant individual body, the collected leaf was crushed, target chlorophyll was extracted with use of a predetermined organic solvent and a total chlorophyll content was calculated with use of a spectrophotometer.

The tomatoes (Tomimaru Mucho) had an average value of 43.6 μg/cm$^2$, whereas the tomatoes (Reika) had an average value of 37.2 μg/cm$^2$. There was a significant difference (P<0.01).

Accordingly, the tomato (Tomimaru Mucho) is regarded as having a chlorophyll content larger than that of the tomato (Reika) and thus is capable of absorbing more light with use of chlorophyll. The tomato (Tomimaru Mucho) is presumed to have a photosynthetic function higher than that of the tomato (Reika).

(Comparison by the Device According to the Present Invention)

The device according to the present invention was used to check a difference in photosynthetic function between these two breeds.

Initially, with use of ten individual bodies for each of the breeds, the device according to the present invention formed an induction curve for each of the individual bodies, and formed a normalized induction curve for each of the breeds.

Figure 5:
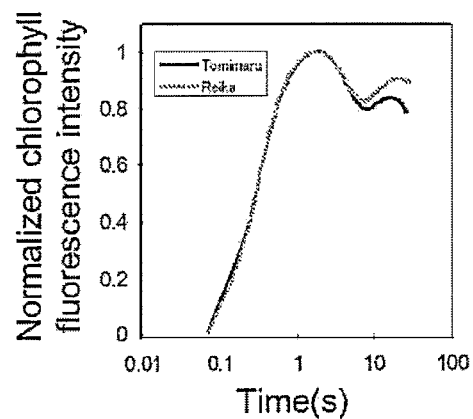
FIGS. 5(A) to 5(C) are graphs indicating test results of evaluation of photosynthetic functions of different breeds.
Figure 5:
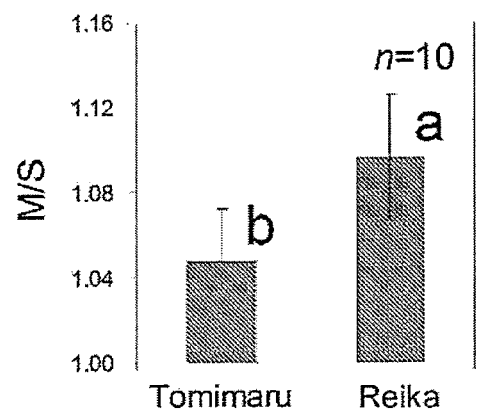
Figure 5:
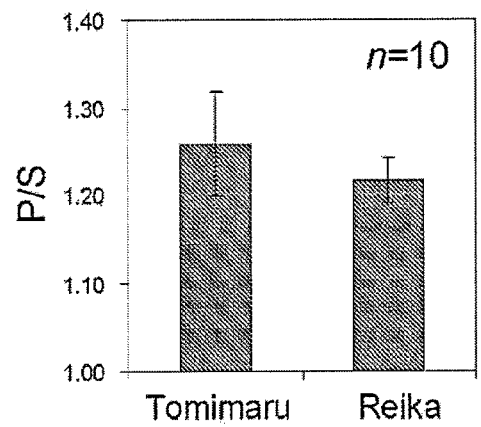

As indicated in FIG. 5(A), on the normalized induction curves for these breeds, there was detected a difference in shape from the first minimum point s after the maximum point p to the first maximum point m after the minimum point s. From the difference in shape between the induction curves formed by the device according to the present invention, confirmed was that there is a difference in photosynthetic function between these breeds.

(Comparison of M/S Values and P/S Values)

M/S values and P/S values were calculated with use of the induction curves for these breeds, so as to compare average values between the two breeds.

As indicated in FIG. 5(B), there was recognized a significant difference between the M/S value (0.94) for the tomato (Reika) and the M/S value (0.91) for the tomato (Tomimaru Mucho) (P<0.01).

The P/S values for these breeds were evaluated in a similar manner.

As indicated in FIG. 5(C), there was recognized no significant difference between the P/S value for the tomato (Tomimaru Mucho) and the P/S value for the tomato (Reika), but the value for the tomato (Tomimaru Mucho) is larger (P<0.10).

It was thus confirmed that the device according to the present invention is capable of detecting the difference in photosynthetic function between the two bleeds in accordance with the M/S values or the P/S values.

(Comparison of Chlorophyll a/b Ratio)

Tested next was whether or not a difference in photosynthetic function between the breeds can be detected in accordance with a chlorophyll a/b ratio, which has been conventionally used as a numerical index for evaluation of a photosynthetic function.

A chlorophyll a/b ratio was calculated in the method similar to the case of the total chlorophyll content (the method according to Porra et al. (1989)).

With use of twelve tomatoes (Tomimaru Mucho) and seven tomatoes (Reika), a chlorophyll a/b ratio in an unit area in a leaf was calculated for each of these breeds.

As a result, there was recognized no significant difference between an average value of the chlorophyll a/b ratios for the tomatoes (Tomimaru Mucho) and an average value of the chlorophyll a/b ratios for the tomatoes (Reika).

In other words, it was impossible to detect a difference in photosynthetic function between the two breeds in accordance with the chlorophyll a/b ratio as a numerical index particularly for light collection capability in the photosynthetic function.

(Comparison of Light-Response Curves)

Tested next was whether or not a difference in photosynthetic function between the breeds can be detected in accordance with a conventional technique for evaluation of a photosynthetic function with use of a light-photosynthesis curve, which is obtained by measuring CO2 absorption speed (photosynthesis speed) with varied light intensity.

Six tomatoes (Tomimaru Mucho) and six tomatoes (Reika) were used to measure light-photosynthesis curves (light-response curves). These light-response curves were formed with use of a handy photosynthesis transpiration measurement device (manufactured by LI-COR, model number: LI-6400) for measuring a state of photosynthesis speed. As to measurement conditions, with use of leaves located in upper portions of the plant bodies, photosynthetic rate was measured at each of PPFD: 0, 50, 250, 500, and 1000 μmol m$^{-2}$s$^{-1}$.

As a result, there was recognized no clear difference between an averaged light-response curve for the tomatoes (Tomimaru Mucho) and an averaged light-response curve for the tomatoes (Reika).

In other words, it was impossible to detect a difference in photosynthetic function between the two breeds in accordance with the light-response curve from which a state of a photosynthetic function can be found in accordance with a difference in photosynthesis speed.

From these results, the device according to the present invention was confirmed to be capable of detecting a slight difference in photosynthetic function between the different breeds, which cannot be detected with use of a conventional method or a conventional device for measuring a state of a photosynthetic function.

In other words, it was confirmed that a slight difference in photosynthetic function between difference breeds can be clearly detected in accordance with the M/S values or the P/S values calculated by the device according to the present invention.

In addition, the device according to the present invention is capable of measuring for about 20 seconds, which is shorter than a time period necessary for measurement of a photosynthetic function in a conventional method. The analysis can be automated completely. It is thus configured that a difference in photosynthetic function can be detected more quickly and more accurately.

(2) A Difference in Photosynthetic Function Between Different Sites in an Identical Individual Body Checked was that a difference in photosynthetic function between different sites (a stem portion and a leaf portion) in an identical individual body can be detected in accordance with M/S values and P/S values calculated by the device according to the present invention.

In order to eliminate influence by variation in light intensity of excitation light applied to chlorophyll, each induction curve was normalized such that the largest chlorophyll fluorescence intensity value P at the maximum point p is equalized with 1. It is possible to easily find a difference in shape of the normalized induction curves.

(Comparison by the Device According to the Present Invention)

With use of two tomatoes (Reika), the device according to the present invention initially specified regions of three leaf portions and three stem portions with use of the chlorophyll fluorescence image processing program in image data of chlorophyll fluorescence measured for each of the individual bodies, and formed an induction curve for each site. Subsequently, there were formed averaged induction curves by averaging the induction curves for the stem portions and the induction curves for the leaf portions.

Figure 6:
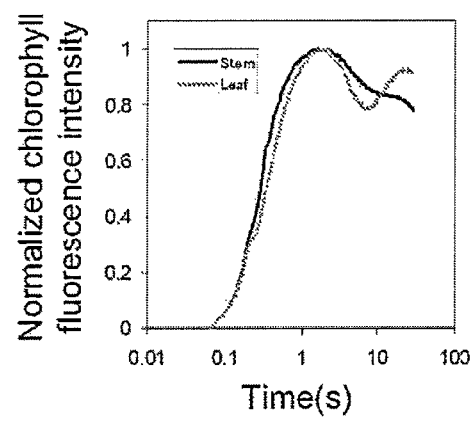
FIGS. 6(A) to 6(C) are graphs indicating test results of evaluation of photosynthetic functions of a stem portion and a leaf portion in an identical plant individual body.
Figure 6:
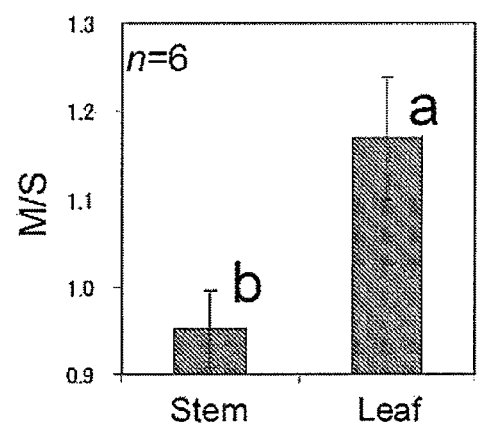
Figure 6:
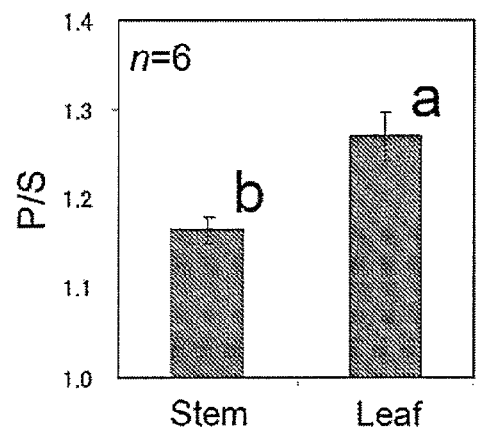

As indicated in FIG. 6(A), on the normalized induction curves for these sites, there was recognized a clear difference in shape from the first minimum point s after the maximum point p to the first maximum point m after the minimum point s. From the difference in shape between the induction curves formed by the device according to the present invention, confirmed was that there is a difference in photosynthetic function between these sites in the identical individual body.

(Comparison of M/S Values and P/S Values)

M/S values and P/S values were calculated with use of the induction curves for these sites, so as to compare average values between the two sites.

As indicated in FIG. 6(B), there was recognized a significant difference between the M/S value (0.95) for the stem portion and the M/S value (1.17) for the leaf portion (P<0.01).

The P/S values for these sites were evaluated in a similar manner.

As indicated in FIG. 6(C), there was recognized a significant difference between the P/S value (1.16) for the stem portion and the P/S value (1.27) for the leaf portion (P<0.01).

It was thus confirmed that the device according to the present invention is capable of detecting the difference in photosynthetic function between these sites in the identical individual body in accordance with the M/S values or the P/S values.

(Comparison of Fv/Fm Values)

Tested next was whether or not a difference in photosynthetic function between these sites can be detected in accordance with the pulse amplitude modulation (PAM) chlorophyll fluorescence measurement method, which has been conventionally used for mainly measuring a photosynthetic electron transport yield.

Used as a chlorophyll fluorescence measurement device in accordance with the pulse amplitude modulation chlorophyll fluorescence measurement method was a handy chlorophyll fluorescence measurement device (manufactured by Walz, model number: MINI-PAM).

With use of ten tomatoes (Reika), the handy chlorophyll fluorescence measurement device (MINI-PAM) calculated Fv/Fm values for stem portions and leaf portions of ten individual bodies, and then calculated average values for the stem portions and the leaf portions.

As a result, there was recognized no significant difference between the average value of the Fv/Fm values for the stem portions and the average value of the Fv/Fm values for the leaf portions of the tomatoes (Reika).

It was impossible to detect a difference in photosynthetic function between these sites in the identical plant individual body in accordance with the Fv/Fm value, which has been regarded as useful for finding a state of a photosynthetic function from a photosynthesis activity ratio (a maximum value of energy used for photosynthesis photochemical reaction out of absorbed light energy in a photosynthetic electron transport system), in other words, photosynthesis capability.

From this result, the device according to the present invention was confirmed to be capable of detecting a slight difference in photosynthetic function between the stem portion and the leaf portion in the identical plant individual body, which could not be detected from Fv/Fm as a fluorescence parameter widely used as an index indicating capability of a photosynthetic reaction system.

More specifically, the device according to the present invention could detect a slight difference in photosynthetic function between the leaf portion as a photosynthetic organ for mainly conducting photosynthesis and the stem portion hardly functioning as a photosynthetic organ. Confirmed was that the device according to the present invention is capable of discriminating between a stem portion and a leaf portion in a plant individual body.

(3) Possibility of Diagnosis in an Early Stage of Disorder by Pests

Prior to check of possibility of diagnosis in an early stage of disorder by pests with use of an actually cultivated plant (hereinafter, referred to as a main test), checked by a preliminary test was whether or not the device according to the present invention enables diagnosis in an early stage with use of a leaf artificially provided with disorder and a leaf having natural physiological disorder.

(I) Preliminary Test

As artificial disorder, there were conducted (a) a photosynthesis inhibitor administration test and (b) a physically damaging test. In order to detect natural physiological disorder, there was conducted (c) a physiological disorder test. A main test was conducted to test whether or not it is possible to conduct diagnosis of disorder in an early stage.

In the preliminary test, a surface of a leaf was captured by a CCD camera of the device according to the present invention. There was formed a chlorophyll fluorescence image for the captured image. An M/S value and a P/S value were calculated for each pixel in accordance with this chlorophyll fluorescence image.

Used as a target of the preliminary test was a leaf of a tomato (TY Momotaro Sakura) planted in a greenhouse. The leaf used for this test was confirmed that it was collected from a healthy matured individual body in a period of stable photosynthesis and had no visible damage.

Figure 7:
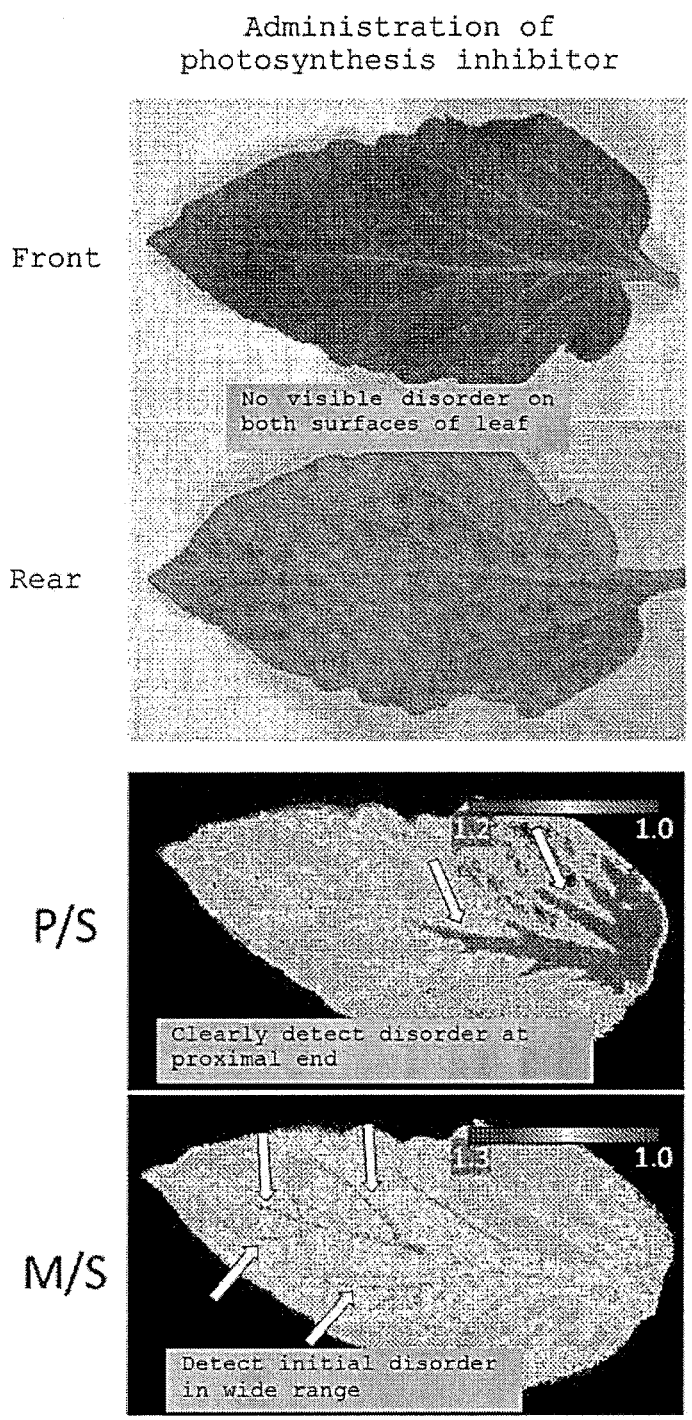
FIG. 7 includes images showing results of a preliminary test (photosynthesis inhibitor administration test) for evaluation of a photosynthetic function of a leaf.
Figure 8:
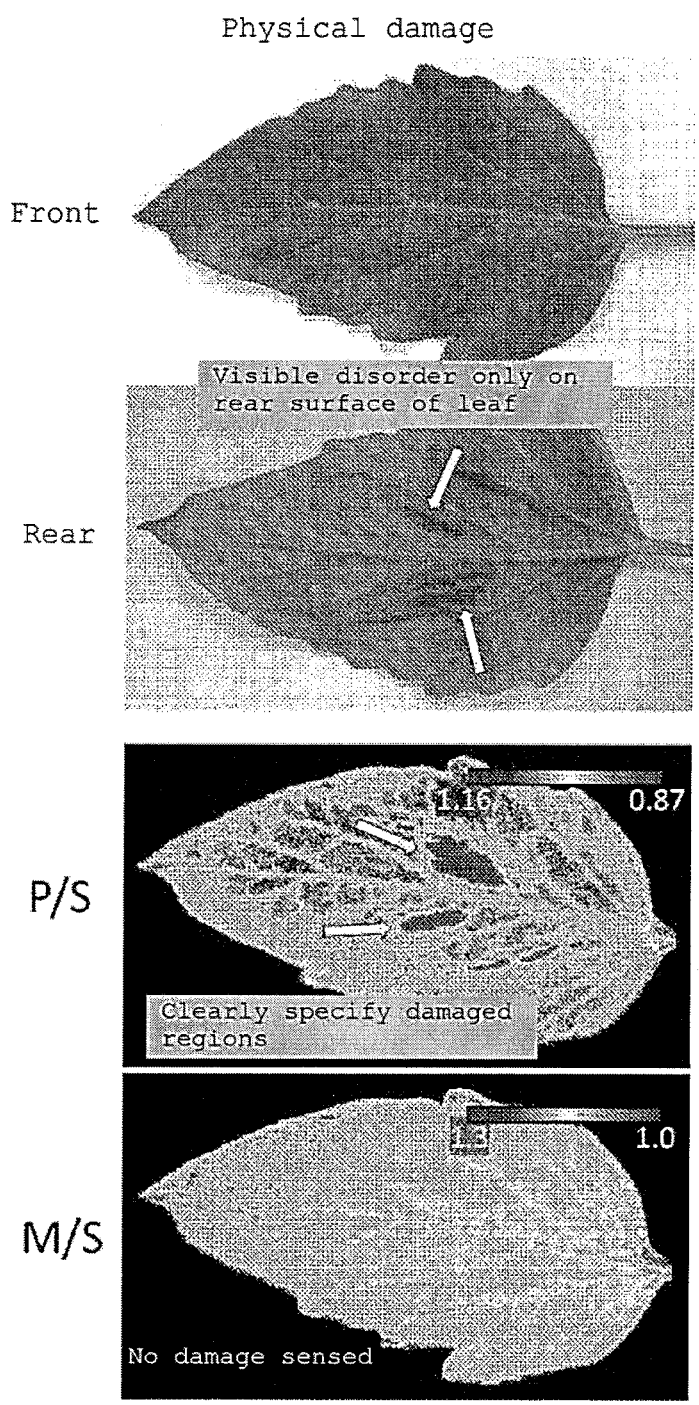
FIG. 8 includes images showing results of a preliminary test (physical damage test) for evaluation of a photosynthetic function of a leaf.
Figure 9:
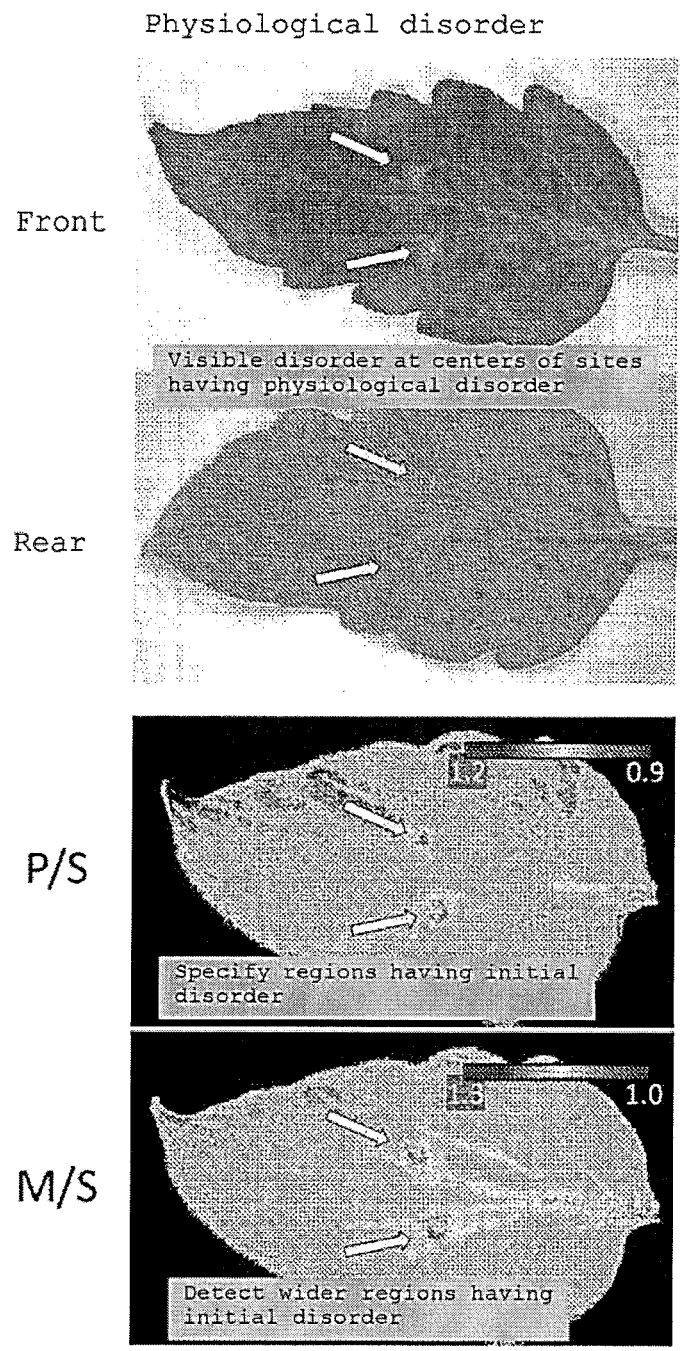
FIG. 9 includes images showing results of a preliminary test (physiological disorder test) for evaluation of a photosynthetic function of a leaf.

The device according to the present invention formed an M/S image and a P/S image colored such that portions having values similar to an M/S value and a P/S value for a reference healthy site are in blue and portions having M/S values and P/S values smaller (in other words, with higher degrees of disorder in photosynthetic function) than these reference values are gradually changed from blue to yellow, and yellow to red. It is noted that images in FIGS. 7 to 9 are in black and white and thus sites having disorder are indicated by arrows.

(a) Photosynthesis Inhibitor Administration Test

There was used a leaf expressing disorder in photosynthetic function of cells by applying a photosynthesis inhibitor to plant cells. Tested was whether or not such disorder in photosynthetic function can be detected in accordance with an M/S image and a P/S image formed from M/S values calculated by the device according to the present invention.

In this test, there was used a photosynthesis inhibitor (manufactured by Takeda Garden Products Inc., model number: dyestuff containing 3% of DCMU [3-(3,4-dichlorophenyl)-1,1-dimethyl urea]). Powders of 1 g of this photosynthesis inhibitor were diluted with 100 ml of tap water to prepare photosynthesis inhibitor solution. A leafstalk of the leaf of the tomato was immersed in this photosynthesis inhibitor solution and was remained for a predetermined period of time, so that the leaf absorbed the photosynthesis inhibitor solution via the leafstalk. The leaf after elapse of the predetermined period of time was difficult to be visually distinguished from a healthy leave, but had disorder in photosynthetic function inside cells of the leaf due to the photosynthesis inhibitor absorbed via the leafstalk.

As a result, as indicated in the P/S image in FIG. 7, it was possible to clearly detect, in the P/S image, regions having remarkably deteriorated photosynthetic functions at the proximal end of the leaf (sites indicated by the arrows in the P/S image in FIG. 7).

On the other hand, as in the M/S image in FIG. 7, it was possible to detect, in the M/S image, photosynthetic functions expanding along veins to the distal end of the leaf, in addition to the proximal end of the leaf (sites indicated by the arrows in the M/S image in FIG. 7).

Confirmed was that it is possible to detect clear disorder in photosynthetic function with use of the P/S image, whereas it is possible to detect initial disorder in photosynthetic function with use of the M/S image, in other words, initial disorder in a wider range in comparison to the P/S image.

(b) Physical Damage Test

There was used a leaf having disorder in photosynthetic function of cells by physically damaging plant cells. Tested was whether or not such disorder in photosynthetic function can be detected in accordance with an M/S image and a P/S image formed from M/S values calculated by the device according to the present invention.

As indicated by the arrows on the rear surface of the leaf in FIG. 8, the rear surface of the healthy leaf was artificially damaged to express damage by pests on the rear surface of the leaf. It was impossible to visually recognize such damage from the front surface of the leaf.

As a result, as indicated in the P/S image in FIG. 8, it was possible to clearly detect, in the P/S image, damaged regions formed on the rear surface of the leaf (sites indicated by the arrows in the P/S image in FIG. 8).

On the other hand, as indicated in the M/S image in FIG. 8, it was difficult to detect, in the M/S image, damaged regions formed on the rear surface of the leaf.

It is difficult to detect plant cells having no photosynthetic functions (corresponding to a terminal condition brought by pests) with use of the MS image, but it was possible to clearly detect the cells with use of the P/S image. In other words, confirmed was that the device according to the present invention is capable of detecting a leaf having damage by pests on the rear surface of the leaf.

(c) Physiological Disorder Test

There was used a leaf having physiological disorder of plant cells. Tested was whether or not such physiological disorder can be detected in accordance with an M/S image and a P/S image formed from M/S values calculated by the device according to the present invention.

As indicated by the arrows on the front surface and the rear surface of the leaf in FIG. 9, there was used the leaf having spotted physiological disorder. In the spotted sites having physiological disorder, it was possible to visually recognize disorder at the centers, but it was difficult to distinguish the peripheries of the disordered sites from the healthy sites.

As a result, as indicated in the P/S image and the M/S image in FIG. 9, it was possible to detect, in the P/S image and the M/S image, the peripheries of the spotted sites having physiological disorder (sites indicated by the arrows in the P/S image and the M/S image in FIG. 9). In particular, it was possible to detect physiological disorder in a wider range with use of the M/S image, in comparison to the P/S image. More specifically, with use of the M/S image, it was possible to detect further peripheries of the peripheries of the sites having physiological disorder detected by the P/S image. Confirmed was that initial physiological disorder can be detected with use of the P/S image and the M/S image, and there is possibility of detection of further initial physiological disorder with use of the M/S image, in comparison to the P/S image.

Confirmed by the results of these preliminary tests was that the device according to the present invention enables diagnosis in an early stage of disorder due to pests.

In other words, the device according to the present invention was confirmed to enable diagnosis in an early stage of disorder due to pests, because the device according to the present invention is capable of detecting slight difference in photosynthetic function or physiological function from a healthy plant cell in the case where the photosynthetic function or the physiological function of the plant cell is influenced by some disorder (due to pests, for example). In particular, the M/S image is effective for detection of initial disorder in a wide range, while the P/S image is effective for detection of clear disorder.

The following main test was conducted on the basis of the results of the preliminary tests described above.

(II) Main Test

Tested was whether or not it is possible to diagnose in an early stage of disorder by tomato russet mite carried by an actually cultivated tomato. Confirmed as a result was that, with disorder by tomato russet mite on a tomato (Reika), it is possible to detect in an early stage initial disorder on the tomato (Reika) due to tomato russet mite with use of an M/S image formed from M/S values calculated by the device according to the present invention.

The device according to the present invention calculated an M/S value for each pixel from chlorophyll fluorescence images measured by the CCD camera, and formed an M/S image with an M/S value for a leaf portion of a healthy plant individual body being set as a reference value. The healthy individual body was visually confirmed as carrying no tomato russet mite, and the reference value was obtained with use of a healthy matured leaf portion in a period of stable photosynthesis.

The device according to the present invention formed the M/S image colored such that portions having values similar to the M/S value for the reference healthy site are in blue and portions having M/S values smaller (in other words, with higher degrees of disorder in photosynthetic function due to tomato russet mite) than this reference value are gradually changed into red.

With use of six healthy tomatoes (Reika) and six tomatoes (Reika) carrying tomato russet mite at leaf portions, stem portions, and the like as measurement targets, the device according to the present invention formed M/S images.

On the surfaces of the leaf portions having initial disorder due to tomato russet mite in the tomatoes (Reika) carrying tomato russet mite, it was impossible to visually recognize a difference in outer appearance from the healthy leaf portion.

In the M/S image of the plant body having initial disorder by tomato russet mite, it was possible to detect a red portion carrying tomato russet mite.

By comparison between the red portion thus detected and a portion on the rear surface of the leaf carrying a small number of tomato russet mite, these portions were recognized as being located substantially at same positions of the leaf. It was possible to detect initial disorder in photosynthetic function on the tomato (Reika) that has no visible disorder on the front surface of the leaf but carries tomato russet mite on the rear surface of the leaf.

In the M/S image formed by the device according to the present invention for the healthy tomato (Reika), there was recognized no red portion detected as described above.

From this result, confirmed was that the device according to the present invention is capable of finding a site having initial disorder due to tomato russet mite in a plant individual body, which was difficult to be visually recognized from outer appearance.

In other words, confirmed was that the device according to the present invention is capable of detecting even a slight change in photosynthetic function between sites (leaf portions) in an identical plant individual body.

The device according to the present invention calculated P/S values and formed P/S images similarly to the above. Confirmed as a result that a site having disorder due to tomato russet mite in a relatively smaller region could be detected as a red portion in the plant individual body carrying tomato russet mite, which was difficult to be visually recognized.

INDUSTRIAL APPLICABILITY

The plant health diagnostic method and the plant health diagnostic device according to the present invention are suitable for diagnosis of health states of plants in a large-scale plant cultivation field.

DESCRIPTION OF REFERENCE SIGNS m: First maximum point after minimum point s
M: Chlorophyll fluorescence intensity at first maximum point m after minimum point s
p: Maximum point having largest chlorophyll fluorescence intensity on induction curve
P: Chlorophyll fluorescence intensity at maximum point p having largest chlorophyll fluorescence intensity on induction curve
s: First minimum point after maximum point p having largest chlorophyll fluorescence intensity
S: Chlorophyll fluorescence intensity at first minimum point s after maximum point p having largest chlorophyll fluorescence intensity

The invention claimed is:

1. A plant health diagnostic method of diagnosing a health state of a plant in accordance with chlorophyll fluorescence emitted from chlorophyll of a plant body, the method comprising:
    irradiating the plant with light;
    step for measuring as an image the chlorophyll fluorescence intensity at intervals with a CCD camera, and based on the image, constructing an induction curve that is a time course curve of the chlorophyll fluorescence intensity;
    a step for obtaining a first minimum point after a maximum point having largest chlorophyll fluorescence intensity and a first maximum point after the minimum point on the induction curve that is a time course curve of the chlorophyll fluorescence intensity;
    a step for defining chlorophyll fluorescence intensity values at the minimum point and the first maximum point after the minimum point as S and M, respectively;
    a step for obtaining a value M/S from the values S and M; and
    a step for evaluating an initial state of photosynthetic functional disorder of the plant body with use of the value M/S and a value M/S of a healthy site of a plant body or of a healthy plant individual body as a reference value.

2. The plant health diagnostic method according to claim 1, the method further comprising:
    a step for obtaining the maximum point having the largest chlorophyll fluorescence intensity on the induction curve;
    a step for defining a chlorophyll fluorescence intensity value at the maximum point having the largest chlorophyll fluorescence intensity as P;
    a step for obtaining a value P/S from the values P and S; and
    a step for evaluating an initial state of photosynthetic functional disorder of the plant body with use of the value P/S and a value P/S of a healthy site of a plant body or of a healthy plant individual body as a reference value.

3. The plant health diagnostic method according to claim 1, wherein
    the initial state of photosynthetic functional disorder is not visually detected.

4. A plant health diagnostic device for diagnosing a health state of a plant in accordance with chlorophyll fluorescence emitted from chlorophyll of a plant body, the device comprising:
    fluorescence measurement means for measuring intensity of the chlorophyll fluorescence; and
    analysis means for evaluating the state of the plant in accordance with the chlorophyll fluorescence intensity measured by the fluorescence measurement means; wherein
    the analysis means
    obtains a first minimum point after a maximum point having largest chlorophyll fluorescence intensity and a first maximum point after the minimum point on a time course curve of the chlorophyll fluorescence intensity measured by the fluorescence measurement means,
    defines chlorophyll fluorescence intensity values at the minimum point and the first maximum point after the minimum point as S and M, respectively,
    obtains a value M/S from the values S and M, and
    evaluates an initial state of photosynthetic functional disorder of the plant body with use of the value M/S and a value M/S of a healthy site of a plant body or of a healthy plant individual body as a reference value.

5. The plant health diagnostic device according to claim 4, wherein
    the analysis means
    obtains the maximum point having the largest chlorophyll fluorescence intensity on the time course curve of the chlorophyll fluorescence intensity measured by the fluorescence measurement means,
    defines a chlorophyll fluorescence intensity value at the maximum point as P,
    obtains a value P/S from the values P and S, and
    evaluates an initial state of photosynthetic functional disorder of the plant body with use of the value P/S and a value P/S of a healthy site of a plant body or of a healthy plant individual body as a reference value.

6. The plant health diagnostic device according to claim 4, wherein
    the fluorescence measurement means
    measures the chlorophyll fluorescence intensity as an image, and the analysis means
    forms an M/S image and/or a P/S image configured by the value M/S and/or the value P/S in accordance with the image of the measured chlorophyll fluorescence intensity, and evaluates an initial state of photosynthetic functional disorder of the plant body with use of the M/S image and/or the P/S image thus formed and an M/S image and/or a P/S image of a healthy site of a plant body or of a healthy plant individual body as a reference image.

7. The plant health diagnostic device according to claim 4, wherein the initial state of photosynthetic functional disorder is not visually detected.

8. A plant health diagnostic method of diagnosing a health state of a plant in accordance with chlorophyll fluorescence emitted from chlorophyll of a plant body, the method comprising:

irradiating the plant with light;

step for measuring as an image the chlorophyll fluorescence intensity at intervals with a CCD camera, and based on the image, constructing an induction curve that is a time course curve of the chlorophyll fluorescence intensity;

a step for obtaining a first minimum point after a maximum point having largest chlorophyll fluorescence intensity and a first maximum point after the minimum point on the induction curve that is a time course curve of the chlorophyll fluorescence intensity;

a step for defining chlorophyll fluorescence intensity values at the minimum point and the first maximum point after the minimum point as S and M, respectively;

a step for obtaining a value M/S from the values S and M;

a step for discriminating a leaf portion and a stem portion in the plant with use of the value M/S; and a step for diagnosing a growth state of the plant in accordance with a stem diameter of the discriminated stem portion.

9. The plant health diagnostic method according to claim 8, the method further comprising:

a step for obtaining the maximum point having the largest chlorophyll fluorescence intensity on the induction curve;

step for defining a chlorophyll fluorescence intensity value at the maximum point having the largest chlorophyll fluorescence intensity as P;

a step for obtaining a value P/S from the values P and S;

a step for discriminating a leaf portion and a stem portion in the plant with use of the value P/S; and a step for diagnosing a growth state of the plant in accordance with a stem diameter of the discriminated stem portion.

10. The plant health diagnostic method according to claim 2, wherein the initial state of photosynthetic functional disorder is not visually detected.

11. The plant health diagnostic device according to claim 5, wherein the fluorescence measurement means measures the chlorophyll fluorescence intensity as an image, and the analysis means forms an M/S image and/or a P/S image configured by the value M/S and/or the value P/S in accordance with the image of the measured chlorophyll fluorescence intensity, and evaluates an initial state of photosynthetic functional disorder of the plant body with use of the M/S image and/or the P/S image thus formed and an M/S image and/or a P/S image of a healthy site of a plant body or of a healthy plant individual body as a reference image.

12. The plant health diagnostic device according to claim 5, wherein the initial state of photosynthetic functional disorder is not visually detected.

13. The plant health diagnostic device according to claim 6, wherein the initial state of photosynthetic functional disorder is not visually detected.

14. The plant health diagnostic device according to claim 11, wherein the initial state of photosynthetic functional disorder is not visually detected.

* * * * *